(12) United States Patent
Inoue et al.

(10) Patent No.: US 9,260,463 B2
(45) Date of Patent: Feb. 16, 2016

(54) SUBSTITUTED PYRIMIDINATO IRIDIUM COMPLEXES AND SUBSTITUTED PYRAZINATO IRIDIUM COMPLEXES HAVING AN ALICYCLIC DIKETONE LIGAND

(71) Applicant: Semiconductor Energy Laboratory Co., Ltd., Kanagawa-ken (JP)

(72) Inventors: Hideko Inoue, Kanagawa (JP); Hiromi Seo, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 166 days.

(21) Appl. No.: 13/688,688

(22) Filed: Nov. 29, 2012

(65) Prior Publication Data
US 2013/0137866 A1    May 30, 2013

(30) Foreign Application Priority Data

Nov. 30, 2011   (JP) .................................. 2011-261289

(51) Int. Cl.
C01G 55/00 (2006.01)
C07F 15/00 (2006.01)

(52) U.S. Cl.
CPC .................................. C07F 15/0033 (2013.01)

(58) Field of Classification Search
CPC ....................................................... C01G 55/00
USPC .............................. 544/296, 335, 336; 423/22
See application file for complete search history.

(56) References Cited

U.S. PATENT DOCUMENTS

| | | | |
|---|---|---|---|
| 6,097,147 A | 8/2000 | Baldo et al. | |
| 6,830,828 B2 | 12/2004 | Thompson et al. | |
| 6,902,830 B2 | 6/2005 | Thompson et al. | |
| 7,001,536 B2 | 2/2006 | Thompson et al. | |
| 7,291,406 B2 | 11/2007 | Thompson et al. | |
| 7,442,448 B2 * | 10/2008 | Kim et al. | 428/690 |
| 7,537,844 B2 | 5/2009 | Thompson et al. | |
| 7,807,839 B2 | 10/2010 | Inoue et al. | |
| 7,883,787 B2 | 2/2011 | Thompson et al. | |
| 7,968,215 B2 * | 6/2011 | Begley et al. | 428/690 |
| 8,071,226 B2 * | 12/2011 | Je et al. | 428/690 |
| 8,084,145 B2 | 12/2011 | Inoue et al. | |
| 8,247,086 B2 | 8/2012 | Inoue et al. | |
| 8,389,982 B2 * | 3/2013 | Kishino et al. | 257/40 |
| 2005/0221123 A1 | 10/2005 | Inoue et al. | |
| 2007/0129545 A1 | 6/2007 | Inoue et al. | |
| 2007/0244320 A1 | 10/2007 | Inoue et al. | |
| 2009/0015143 A1 | 1/2009 | Inoue et al. | |
| 2010/0105902 A1 | 4/2010 | Inoue et al. | |
| 2011/0057560 A1 | 3/2011 | Inoue et al. | |
| 2011/0082296 A1 | 4/2011 | Inoue et al. | |
| 2011/0112296 A1 | 5/2011 | Thompson et al. | |
| 2012/0098417 A1 | 4/2012 | Inoue et al. | |
| 2012/0274201 A1 | 11/2012 | Seo et al. | |
| 2013/0088144 A1 | 4/2013 | Inoue et al. | |

FOREIGN PATENT DOCUMENTS

| | | | |
|---|---|---|---|
| EP | 1434286 | * | 6/2004 |
| JP | 2007-137872 | | 6/2007 |
| JP | 2008-69221 | | 3/2008 |
| KR | 2011077173 | * | 7/2011 |
| TW | I231157 B | | 4/2005 |
| WO | WO 00/70655 A2 | | 11/2000 |
| WO | WO 2006028224 | * | 3/2006 |
| WO | WO 2008/035664 A1 | | 3/2008 |
| WO | WO 2008101842 | * | 8/2008 |
| WO | WO 2010074087 | * | 7/2010 |

OTHER PUBLICATIONS

Luo, et al., Faguang Xuebao (2011), 32(4), 368-373.*
Wang, et al. (I), Dalton Transactions (2011), 40(19), 5166-5169.*
Wang, et al. (II), Molecular Crystals and Liquid Crystals (2009), 499, 340-347.*
Huang, et al., Chemical Communications (Cambridge, U. K.) (2009), (10), 1243-1245.*
Kim, et al. (III), Molecular Crystals and Liquid Crystals (2004), 424, 111-117.*
Bredereck, H. et al., "Formamide Reactions, VIII. A New Pyrimidine-Synthesis," Chemische Berichte, vol. 90, 1957, pp. 942-952 (with full English translation).
Kawanishi, Y. et al., "Dependence of Spectroscopic, Electrochemical, and Excited-State Properties of Tris Chelate Ruthenium(II) Complexes on Ligand Structure," Inorganic Chemistry, vol. 28, No. 15, 1989, pp. 2968-2975.
Caygill, G.B. et al., "Cyclometallated Compounds IV. Cyclopalladation of Phenylpyrimidines and X-ray Structure of a Doubly Cyclopalladated Derivative of 4,6-diphenylpyrimidine,", Journal of Organometallic Chemistry, Feb. 13, 1990, vol. 382, No. 3, pp. 455-469.

(Continued)

*Primary Examiner* — Douglas M Willis
(74) *Attorney, Agent, or Firm* — Husch Blackwell LLP

(57) ABSTRACT

As a novel substance having a novel skeleton, a novel organometallic complex that can emit phosphorescence in the green to red wavelength region and has high emission efficiency and a high yield of synthesis is provided. One embodiment of the present invention is an organometallic complex in which a diketone having a five-membered or six-membered alicyclic structure composed of carbon and hydrogen is a ligand.

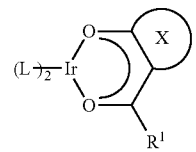

(G1)

In the formula, L represents a bidentate aromatic ligand and has at least a bond between carbon of an aromatic ring in the aromatic ligand and Ir. X represents a five-membered or six-membered alicycle composed of carbon and hydrogen. Further, $R^1$ represents a substituted or unsubstituted alkyl group having 1 to 4 carbon atoms.

13 Claims, 26 Drawing Sheets

(56) References Cited

OTHER PUBLICATIONS

Niu, Y.-H. et al., "Highly Efficient Red Electrophosphorescent Devices Based on an Iridium Complex with Trifluoromethyl-Substituted Pyrimidine Ligand," Applied Physics Letters, vol. 85, No. 9, Aug. 30, 2004, pp. 1619-1621.

Kozhevnikov, V.N. et al., "Highly Luminescent Mixed-Metal Pt(II)/Ir(III) Complexes: Bis-Cyclometalation of 4,6-Diphenylpyrimidine as a Versatile Route to Rigid Multimetallic Assemblies," Inorganic Chemistry, vol. 50, No. 13, 2011, pp. 6304-6313.

* cited by examiner

SUBSTITUTED PYRIMIDINATO IRIDIUM COMPLEXES AND SUBSTITUTED PYRAZINATO IRIDIUM COMPLEXES HAVING AN ALICYCLIC DIKETONE LIGAND

BACKGROUND OF THE INVENTION

1. Field of the Invention

One embodiment of the present invention relates to an organometallic complex. In particular, one embodiment of the present invention relates to an organometallic complex that is capable of converting a triplet excited state into luminescence. In addition, one embodiment of the present invention relates to a light-emitting element, a light-emitting device, an electronic device, and a lighting device each using the organometallic complex.

2. Description of the Related Art

Organic compounds are brought into an excited state by the absorption of light. Through this excited state, various reactions (photochemical reactions) are caused in some cases, or luminescence is generated in some cases. Therefore, the organic compounds have a wide range of applications.

As one example of the photochemical reactions, a reaction of singlet oxygen with an unsaturated organic molecule (oxygen addition) is known. Since the ground state of an oxygen molecule is a triplet state, oxygen in a singlet state (singlet oxygen) is not generated by direct photoexcitation. However, in the presence of another triplet excited molecule, singlet oxygen is generated to cause an oxygen addition reaction. In this case, a compound capable of forming the triplet excited molecule is referred to as a photosensitizer.

As described above, for generation of singlet oxygen, a photosensitizer capable of forming a triplet excited molecule by photoexcitation is needed. However, the ground state of an ordinary organic compound is a singlet state; therefore, photoexcitation to a triplet excited state is forbidden transition and generation of a triplet excited molecule is difficult. A compound that can easily cause intersystem crossing from the singlet excited state to the triplet excited state (or a compound that allows the forbidden transition of photoexcitation directly to the triplet excited state) is thus required as such a photosensitizer. In other words, such a compound can be used as the photosensitizer and is useful.

The above compound often exhibits phosphorescence. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). Application fields of a compound capable of exhibiting phosphorescence, that is, a compound capable of converting the triplet excited state into luminescence (hereinafter, referred to as a phosphorescent compound), include a light-emitting element including an organic compound as a light-emitting substance.

This light-emitting element has a simple structure in which a light-emitting layer including an organic compound that is a light-emitting substance is provided between electrodes. This light-emitting element has attracted attention as a next-generation flat panel display element in terms of characteristics such as being thin and light in weight, high speed response, and direct current low voltage driving. Further, a display device including this light-emitting element is superior in contrast, image quality, and wide viewing angle.

The light-emitting element including an organic compound as a light-emitting substance has a light emission mechanism that is of a carrier injection type: a voltage is applied between electrodes where a light-emitting layer is interposed, electrons and holes injected from the electrodes recombine to put the light-emitting substance into an excited state, and then light is emitted in returning from the excited state to the ground state. As in the case of photoexcitation described above, types of the excited state include a singlet excited state ($S^*$) and a triplet excited state ($T^*$). The statistical generation ratio thereof in the light-emitting element is considered to be $S^*:T^*=1:3$.

At room temperature, a compound capable of converting a singlet excited state into luminescence (hereinafter, referred to as a fluorescent compound) exhibits only luminescence from the singlet excited state (fluorescence), not luminescence from the triplet excited state (phosphorescence). Accordingly, the internal quantum efficiency (the ratio of the number of generated photons to the number of injected carriers) of a light-emitting element including the fluorescent compound is assumed to have a theoretical limit of 25%, on the basis of $S^*:T^*=1:3$.

On the other hand, in a case of a light-emitting element including the phosphorescent compound described above, the internal quantum efficiency thereof can be improved to 75% to 100% in theory; namely, the emission efficiency thereof can be 3 to 4 times as much as that of the light-emitting element including a fluorescent compound. Therefore, the light-emitting element including a phosphorescent compound has been actively developed in recent years in order to achieve a highly efficient light-emitting element. An organometallic complex that contains iridium or the like as a central metal is particularly attracting attention as a phosphorescent compound because of its high phosphorescence quantum yield (refer to Patent Document 1, Patent Document 2, and Patent Document 3).

REFERENCE

Patent Document

[Patent Document 1] Japanese Published Patent Application No. 2007-137872
[Patent Document 2] Japanese Published Patent Application No. 2008-069221
[Patent Document 3] International Publication WO 2008/035664 Pamphlet

SUMMARY OF THE INVENTION

While blue or green phosphorescent materials have been developed as reported in Patent Documents 1 to 3, what is also important in view of extension of the range of light-emitting materials is development of materials having novel skeletons.

Thus, as a novel substance having a novel skeleton, one embodiment of the present invention provides a novel organometallic complex that can emit phosphorescence in the green to red wavelength region and has high emission efficiency and a high yield of synthesis. One embodiment of the present invention provides a light-emitting element, a light-emitting device, an electronic device, or a lighting device with high emission efficiency.

One embodiment of the present invention is an organometallic complex in which a diketone having a five-membered or six-membered alicyclic structure composed of carbon and hydrogen is a ligand. Therefore, one embodiment of the present invention is an organometallic complex having a structure represented by General Formula (G1).

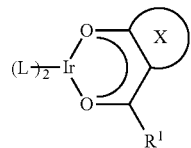

In the formula, L represents a bidentate aromatic ligand and has at least a bond between carbon of an aromatic ring in the aromatic ligand and Ir. X represents a five-membered or six-membered alicycle composed of carbon and hydrogen. Further, $R^1$ represents a substituted or unsubstituted alkyl group having 1 to 4 carbon atoms.

Note that in the above structure, it is preferable that the aromatic ligand be a nitrogen-containing heteroaromatic ring derivative substituted by an aryl group or a nitrogen-containing heterocyclic carbene derivative substituted by an aryl group, and the site of substitution of the aryl group be carbon adjacent to nitrogen atom of nitrogen-containing heteroaromatic ring or nitrogen adjacent to carbene carbon atom.

In the above structure, the aromatic ligand is preferably a ligand represented by any one of General Formulae (L1) to (L3).

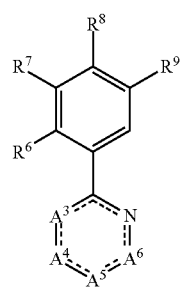

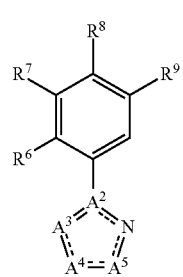

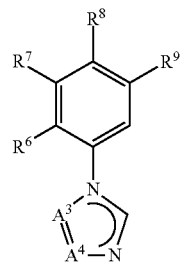

In General Formulae (L1) to (L3), $R^6$ to $R^9$ separately represent hydrogen, a substituted or unsubstituted alkyl group having 1 to 4 carbon atoms, or a substituted or unsubstituted phenyl group. $A^2$ to $A^6$ separately represent oxygen, sulfur, nitrogen, $sp^2$ hybridized nitrogen bonded to any of an alkyl group having 1 to 4 carbon atoms and a phenyl group, $sp^2$ hybridized carbon bonded to hydrogen, or $sp^2$ hybridized carbon bonded to any of an alkyl group having 1 to 4 carbon atoms and a phenyl group. Further, adjacent two atoms of $A^2$ to $A^6$ may be bonded to each other to form a ring.

Another embodiment of the present invention is an organometallic complex represented by General Formula (G2).

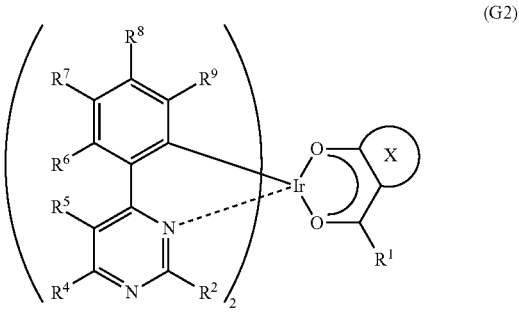

In the formula, X represents a five-membered or six-membered alicycle composed of carbon and hydrogen. $R^1$ represents a substituted or unsubstituted alkyl group having 1 to 4 carbon atoms. Further, $R^2$ and $R^4$ to $R^9$ separately represent a substituted or unsubstituted alkyl group having 1 to 4 carbon atoms, or a substituted or unsubstituted phenyl group.

Another embodiment of the present invention is an organometallic complex represented by General Formula (G3).

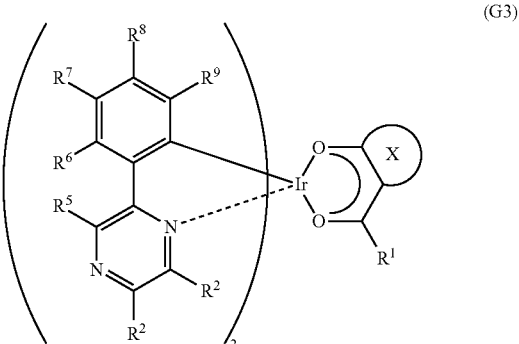

In the formula, X represents a five-membered or six-membered alicycle composed of carbon and hydrogen. $R^1$ represents a substituted or unsubstituted allyl group having 1 to 4 carbon atoms. Further, $R^2$, $R^3$, and $R^5$ to $R^9$ separately represent a substituted or unsubstituted alkyl group having 1 to 4 carbon atoms, or a substituted or unsubstituted phenyl group.

Another embodiment of the present invention is an organometallic complex represented by Structural Formula (100).

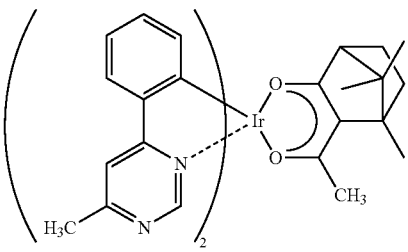

(100)

Another embodiment of the present invention is an organometallic complex represented by Structural Formula (101).

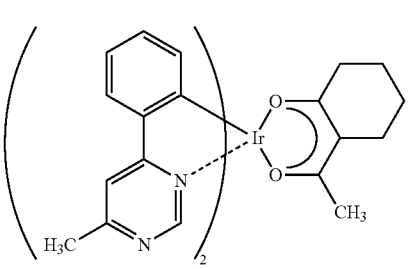

(101)

Another embodiment of the present invention is an organometallic complex represented by Structural Formula (104).

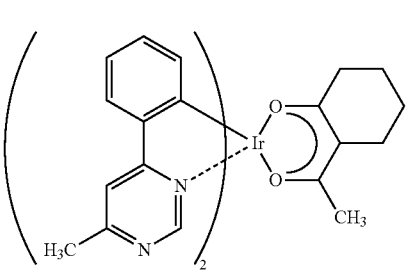

(101)

Another embodiment of the present invention is an organometallic complex represented by Structural Formula (113).

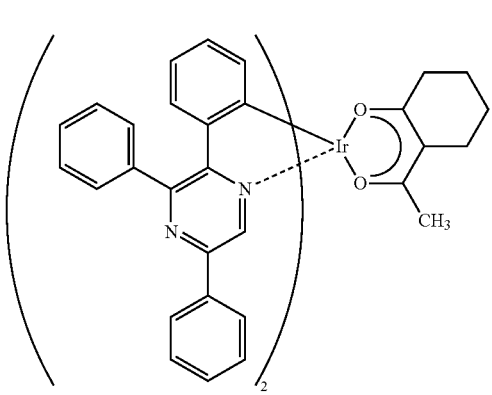

(113)

Further, the organometallic complex of one embodiment of the present invention is very effective for the following reason: the organometallic complex can emit phosphorescence, that is, it can provide luminescence from a triplet excited state and can exhibit emission, and therefore higher efficiency is possible when the organometallic complex is applied to a light-emitting element. Thus, the present invention also includes a light-emitting element in which the organometallic complex of one embodiment of the present invention is used.

Other embodiments of the present invention are not only a light-emitting device including the light-emitting element but also an electronic device and a lighting device each including the light-emitting device. The light-emitting device in this specification refers to an image display device and a light source (e.g., a lighting device). In addition, the light-emitting device includes, in its category, all of a module in which a light-emitting device is connected to a connector such as a flexible printed circuit (FPC) or a tape carrier package (TCP), a module in which a printed wiring board is provided on the tip of a TCP, and a module in which an integrated circuit (IC) is directly mounted on a light-emitting element by a chip on glass (COG) method.

As a novel substance having a novel skeleton, one embodiment of the present invention can provide a novel organometallic complex that can emit phosphorescence in the green to red wavelength region and has high emission efficiency and a high yield of synthesis. Further, since the organometallic complex that is one embodiment of the present invention has the novel skeleton, emission color of phosphorescence to be obtained can also be adjusted. With the use of the novel organometallic complex, a light-emitting element, a light-emitting device, an electronic device, or a lighting device with high emission efficiency can be provided. Alternatively, it is possible to provide a light-emitting element, a light-emitting device, an electronic device, or a lighting device with low power consumption.

DETAILED DESCRIPTION OF THE INVENTION

Figure 1:
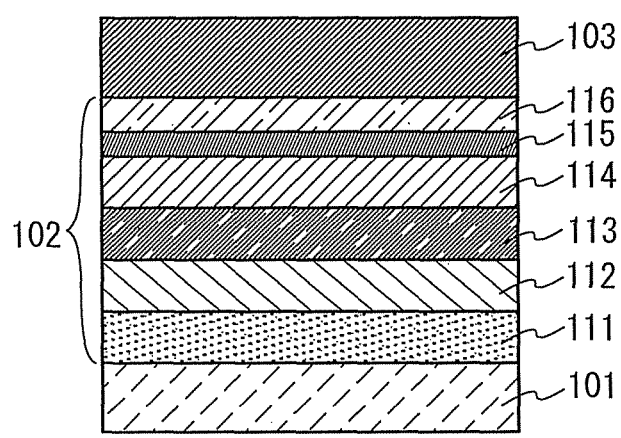
FIG. 1 illustrates a structure of a light-emitting element.

Hereinafter, embodiments of the present invention will be described in detail with reference to the accompanying drawings. Note that the present invention is not limited to the description below, and modes and details thereof can be modified in various ways without departing from the spirit and the scope of the present invention. Therefore, the present invention should not be construed as being limited to the description of the following embodiments.

Embodiment 1

In this embodiment, organometallic complexes which are embodiments of the present invention are described.

An organometallic complex that is one embodiment of the present invention is an organometallic complex in which a diketone having a five-membered or six-membered alicyclic structure composed of carbon and hydrogen is a ligand. Note that one mode of an organometallic complex in which a diketone having a five-membered or six-membered alicyclic structure composed of carbon and hydrogen is a ligand and which is described in this embodiment is an organometallic complex having the structure represented by General Formula (G1).

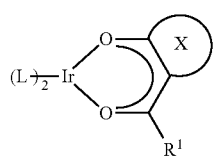

(G1)

In General Formula (G1), L represents a bidentate aromatic ligand and has at least a bond between carbon of an aromatic ring in the aromatic ligand and Ir. X represents a five-membered or six-membered alicycle composed of carbon and hydrogen. Further, $R^1$ represents a substituted or unsubstituted alkyl group having 1 to 4 carbon atoms.

Note that specific examples of the alkyl group having 1 to 4 carbon atoms in $R^1$ include a methyl group, an ethyl group, a propyl group, an isopropyl group, a butyl group, a sec-butyl group, an isobutyl group, and a tert-butyl group.

Specific examples of L that is the bidentate aromatic ligand include a nitrogen-containing heteroaromatic ring derivative substituted by an aryl group and a nitrogen-containing heterocyclic carbene derivative substituted by an aryl group, and it is preferable that the site of substitution of the aryl group be carbon adjacent to nitrogen atom of nitrogen-containing heteroaromatic ring or nitrogen adjacent to carbene carbon atom.

Specifically, L that is the bidentate aromatic ligand is preferably a ligand represented by any of General Formulae (L1) to (L3).

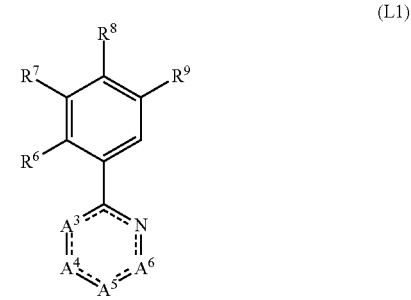

(L1)

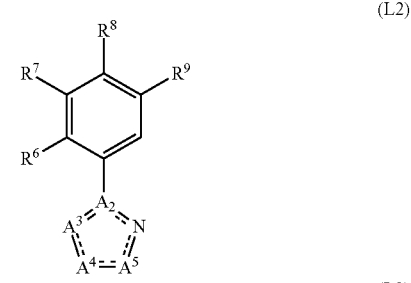

(L2)

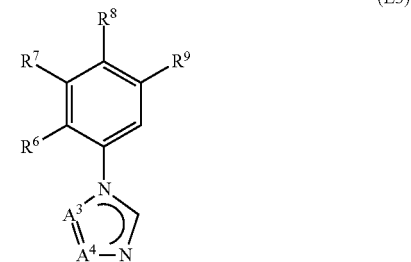

(L3)

In General Formulae (L1) to (L3), $R^6$ to $R^9$ separately represent hydrogen, a substituted or unsubstituted alkyl group having 1 to 4 carbon atoms, or a substituted or unsubstituted phenyl group. $A^2$ to $A^6$ separately represent oxygen, sulfur, nitrogen, $sp^2$ hybridized nitrogen bonded to any of an alkyl group having 1 to 4 carbon atoms and a phenyl group, $sp^2$ hybridized carbon bonded to hydrogen, or $sp^2$ hybridized carbon bonded to any of an alkyl group having 1 to 4 carbon atoms and a phenyl group. Further, adjacent two atoms of $A^2$ to $A^6$ may be bonded to each other to form a ring.

Note that in an organometallic complex that is one embodiment of the present invention, a diketone having a five-membered or six-membered alicyclic structure composed of carbon and hydrogen is a ligand. That is, the ligand has a β-diketone structure, whereby solubility of the organometallic complex in an organic solvent is increased and purification is enhanced, which is preferable. The β-diketone structure is preferably included for realization of an organometallic complex with high emission efficiency. Inclusion of the β-diketone structure has advantages such as a higher sublimation property and excellent evaporativity.

One embodiment of the present invention is an organometallic complex represented by General Formula (G2).

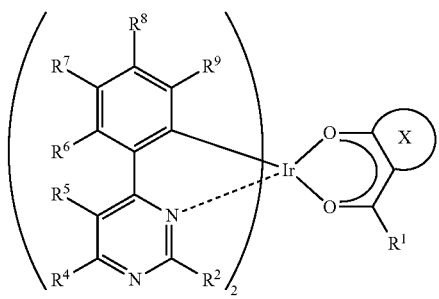

(G2)

In General Formula (G2), X represents a five-membered or six-membered alicycle composed of carbon and hydrogen. $R^1$ represents a substituted or unsubstituted alkyl group having 1 to 4 carbon atoms. Further, $R^2$ and $R^4$ to $R^9$ separately represent a substituted or unsubstituted alkyl group having 1 to 4 carbon atoms, or a substituted or unsubstituted phenyl group. Note that specific examples of $R^1$ are the same as those of $R^1$ in General Formula (G1). Further, specific examples of $R^2$ and $R^4$ to $R^9$ include a phenyl group as well as the specific examples of $R^1$ in General Formula (G1).

One embodiment of the present invention is an organometallic complex represented by General Formula (G3).

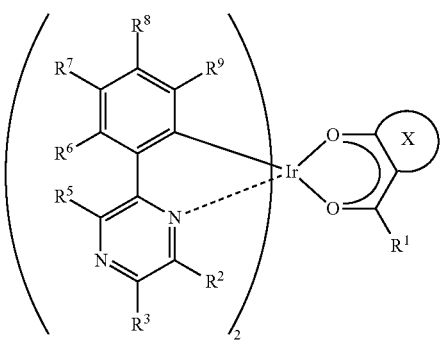

(G3)

In General Formula (G3), X represents a five-membered or six-membered alicycle composed of carbon and hydrogen. $R^1$ represents a substituted or unsubstituted alkyl group having 1 to 4 carbon atoms. $R^2$, $R^3$, and $R^5$ to $R^9$ separately represent a substituted or unsubstituted alkyl group having 1 to 4 carbon atoms, or a substituted or unsubstituted phenyl group. Note that specific examples of $R^1$ are the same as those of $R^1$ in General Formula (G1). Further, specific examples of $R^2$, $R^3$, and $R^5$ to $R^9$ include a phenyl group as well as the specific examples of $R^1$ in General Formula (G1).

Next, specific structural formulae of the above-described organometallic complexes each of which is one embodiment of the present invention will be shown (Structural Formulae (100) to (123)). Note that the present invention is not limited thereto.

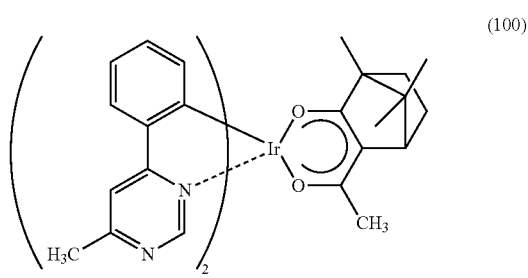

(100)

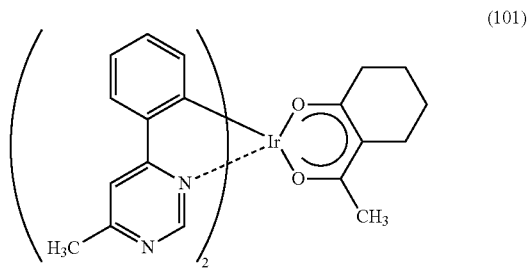

(101)

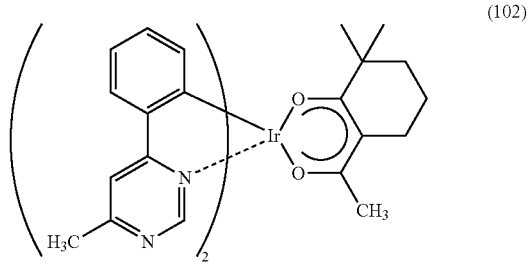

(102)

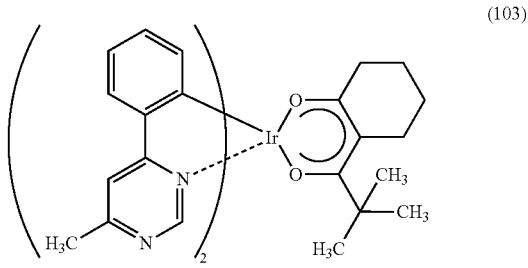

(103)

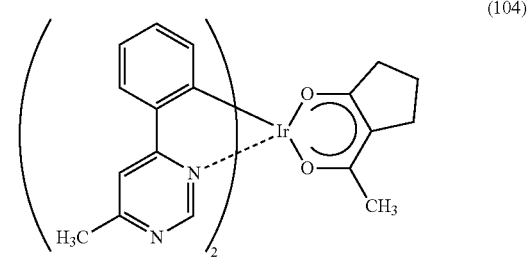

(104)

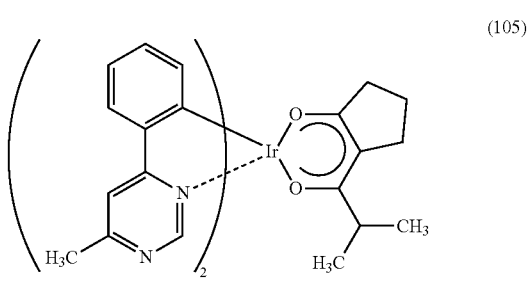

(105)

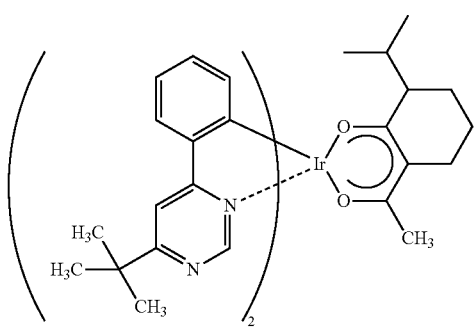
(106)
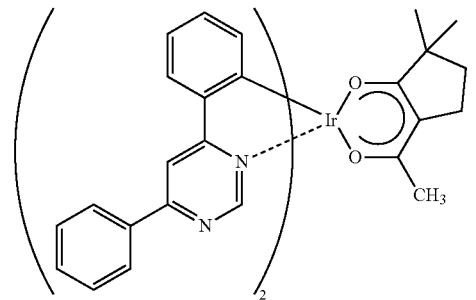
(107)
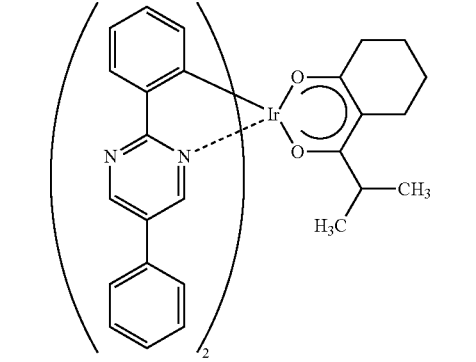
(108)
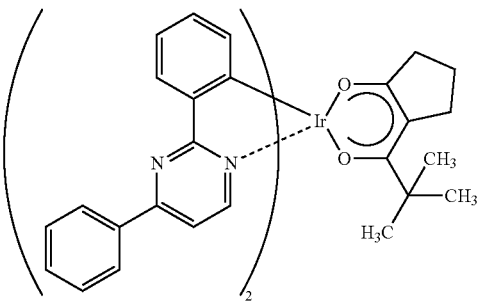
(109)
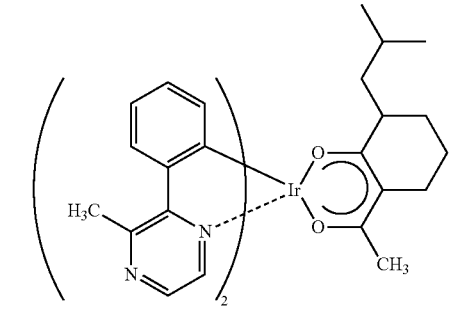
(110)
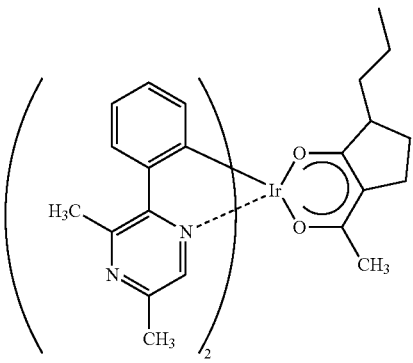
(111)
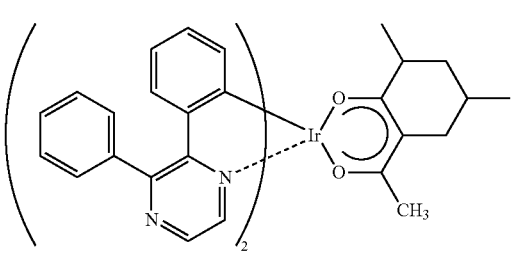
(112)
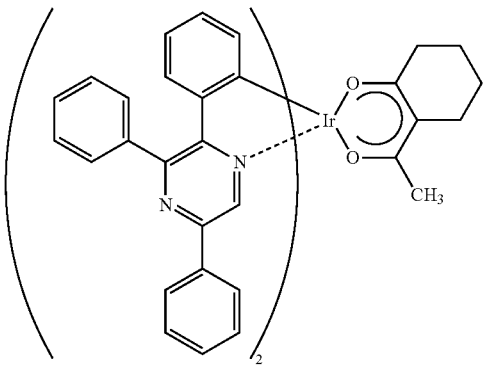
(113)
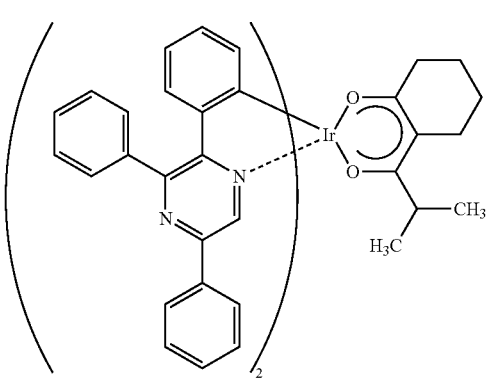
(114)

(115)
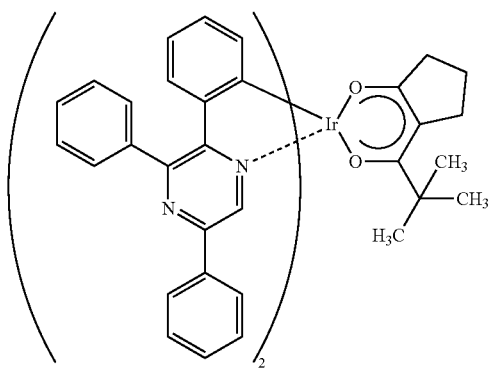

(116)
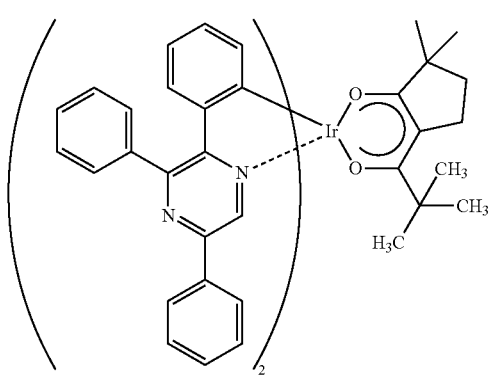

(117)
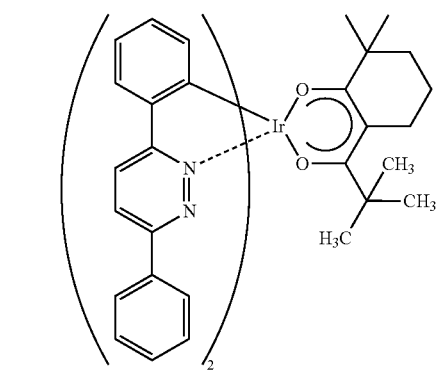

(118)
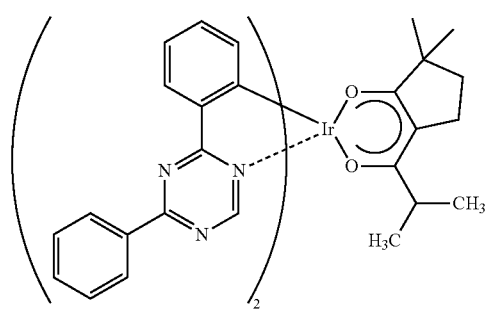

(119)
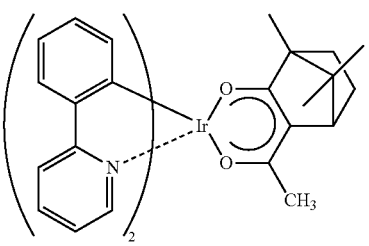

(120)
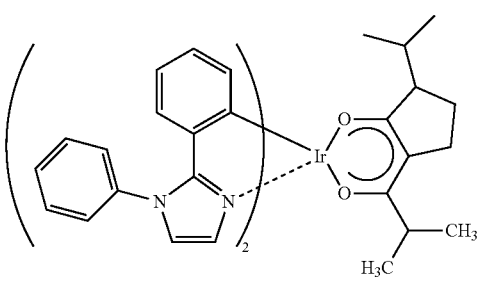

(121)
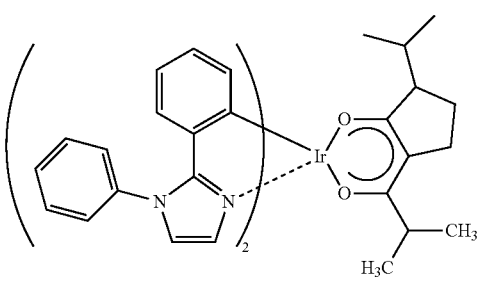

(122)
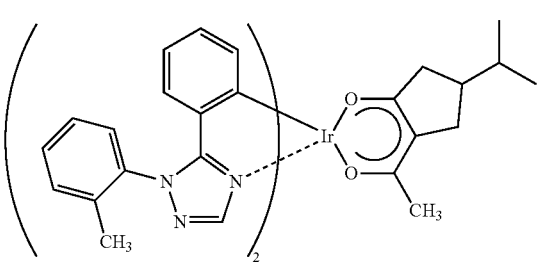

(123)
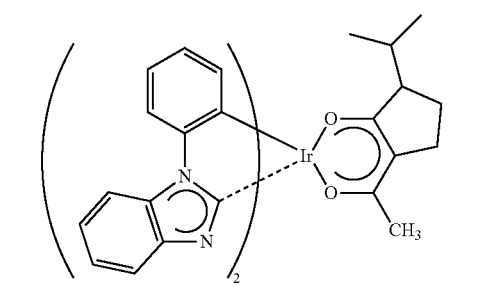

Note that organometallic complexes represented by Structural Formulae (100) to (123) are novel substances capable of emitting phosphorescence. Note that there can be geometrical isomers and stereoisomers of these substances depending on the type of the ligand. The organometallic complex according to one embodiment of the present invention includes all of these isomers.

Next, an example of a method of synthesizing an organometallic complex having the structure represented by General Formula (G1) is described.

Method of Synthesizing β-diketone Derivative Represented by General Formula (G0)

An example of a method of synthesizing a β-diketone derivative represented by General Formula (G0) is described.

(G0)

In General Formula (G0), X represents a five-membered or six-membered alicycle composed of carbon and hydrogen. $R^1$ represents a substituted or unsubstituted alkyl group having 1 to 4 carbon atoms.

Synthesis Scheme (A) of the β-diketone derivative represented by General Formula (G0) is shown below.

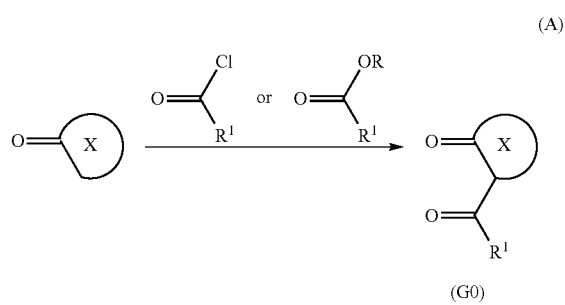

(A)

Note that in Synthesis Scheme (A), a cyclic ketone and a carboxylic acid derivative (e.g., carboxylic acid chloride, carboxylic acid ester, carboxylic acid anhydride, and carboxylic acid amide) are reacted to yield the β-diketone derivative (G0). Note that there are a plurality of known methods of synthesizing the β-diketone derivative (G0), any of which can be employed.

Since the above-described cyclic ketone and carboxylic acid derivative are commercially available or their synthesis is feasible, a great variety of β-diketone derivatives can be synthesized as the β-diketone derivative represented by General Formula (G0). Thus, a feature of the organometallic complex which is one embodiment of the present invention is the abundance of ligand variations.

Method of Synthesizing Organometallic Complex of One Embodiment of the Present Invention Represented by General Formula (G1')

Next, a synthesis method of an organometallic complex represented by General Formula (G1'), in which the bidentate aromatic ligand (L) in the organometallic complex (G1) is the ligand represented by General Formula (L1), will be described. The organometallic complex represented by General Formula (G1') is an example of the organometallic complex (G1) which is formed using the β-diketone derivative represented by General Formula (G0) and which is one embodiment of the present invention.

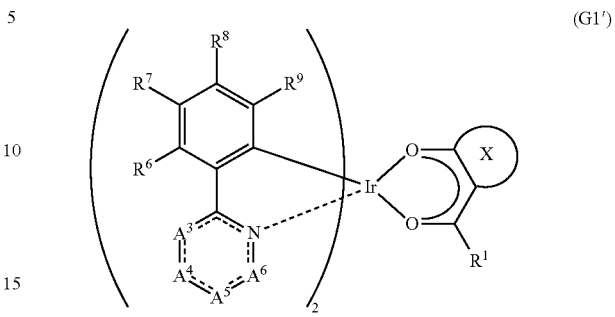

In General Formula (G1'), X represents a five-membered or six-membered alicycle composed of carbon and hydrogen. $R^1$ represents a substituted or unsubstituted alkyl group having 1 to 4 carbon atoms. Further, $R^6$ to $R^9$ separately represent hydrogen, a substituted or unsubstituted alkyl group having 1 to 4 carbon atoms, or a substituted or unsubstituted phenyl group. $A^3$ to $A^6$ separately represent oxygen, sulfur, nitrogen, $sp^2$ hybridized nitrogen bonded to any of an alkyl group having 1 to 4 carbon atoms and a phenyl group, $sp^2$ hybridized carbon bonded to hydrogen, or $sp^2$ hybridized carbon bonded to any of an alkyl group having 1 to 4 carbon atoms and a phenyl group. Further, adjacent two atoms of $A^2$ to $A^6$ may be bonded to each other to form a ring.

Shown below is Synthesis Scheme (B) of the organometallic complex which is represented by General Formula (G1') and in which a diketone having a five-membered or six-membered alicyclic structure composed of carbon and hydrogen is a ligand.

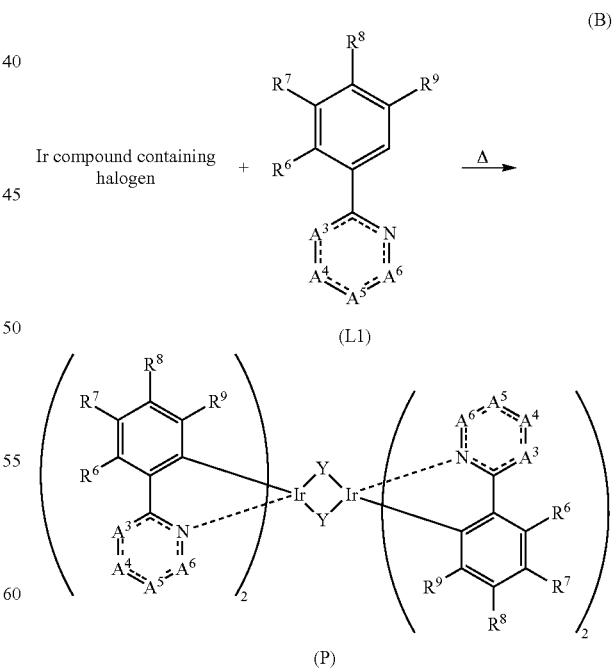

In Synthesis Scheme (B), Y represents a halogen, and $R^6$ to $R^9$ separately represent hydrogen, a substituted or unsubstituted alkyl group having 1 to 4 carbon atoms, or a substituted or unsubstituted phenyl group. $A^3$ to $A^6$ separately represent oxygen, sulfur, nitrogen, $sp^2$ hybridized nitrogen bonded to any of an alkyl group having 1 to 4 carbon atoms and a phenyl group, $sp^2$ hybridized carbon bonded to hydrogen, or $sp^2$ hybridized carbon bonded to any of an alkyl group having 1 to 4 carbon atoms and a phenyl group. Further, adjacent two atoms of $A^3$ to $A^6$ may be bonded to each other to form a ring.

As shown in Synthesis Scheme (B), a bidentate aromatic ligand represented by General Formula (L1) and an Ir compound which contains a halogen (e.g., iridium chloride, iridium bromide, or iridium iodide) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more of the alcohol-based solvents, whereby a dinuclear complex (P), which is one type of an organometallic complex including a halogen-bridged structure, can be obtained.

There is no particular limitation on a heating means, and an oil bath, a sand bath, or an aluminum block may be used. Alternatively, microwaves can be used as a heating means.

Further, as shown in Synthesis Scheme (C), the dinuclear complex (P) obtained in Synthesis Scheme (B) is reacted with the β-diketone derivative represented by General Formula (G0) in an inert gas atmosphere, whereby a proton of the β-diketone derivative represented by General Formula (G0) is eliminated and the β-diketone derivative represented by General Formula (G0) coordinates to the central metal Ir. Thus, the organometallic complex that is one embodiment of the present invention, represented by General Formula (G1'), can be obtained.

In Synthesis Scheme (C), Y represents a halogen, $R^1$ represents a substituted or unsubstituted alkyl group having 1 to 4 carbon atoms, and $R^6$ to $R^9$ separately represent hydrogen, a substituted or unsubstituted alkyl group having 1 to 4 carbon atoms, or a substituted or unsubstituted phenyl group. $A^3$ to $A^6$ separately represent oxygen, sulfur, nitrogen, $sp^2$ hybridized nitrogen bonded to any of an alkyl group having 1 to 4 carbon atoms and a phenyl group, $sp^2$ hybridized carbon bonded to hydrogen, or $sp^2$ hybridized carbon bonded to any of an alkyl group having 1 to 4 carbon atoms and a phenyl group. Further, adjacent two atoms of $A^3$ to $A^6$ may be bonded to each other to form a ring.

There is no particular limitation on a heating means, and an oil bath, a sand bath, or an aluminum block may be used. Alternatively, microwaves can be used as a heating means.

Note that the β-diketone derivative (G0) having the five-membered or six-membered alicyclic structure composed of carbon and hydrogen in General Formula (G1') has a β-diketone structure, whereby solubility of the organometallic complex in an organic solvent is increased and purification is enhanced, which is preferable. The β-diketone structure is preferably included for realization of an organometallic complex with high emission efficiency. Inclusion of the β-diketone structure has advantages such as a higher sublimation property and excellent evaporativity.

The bidentate aromatic ligand is preferably a ligand represented by any one of General Formulae (L1) to (L3). Since these ligands have high coordinative ability, and are inexpensively available or can be synthesized easily, they are useful.

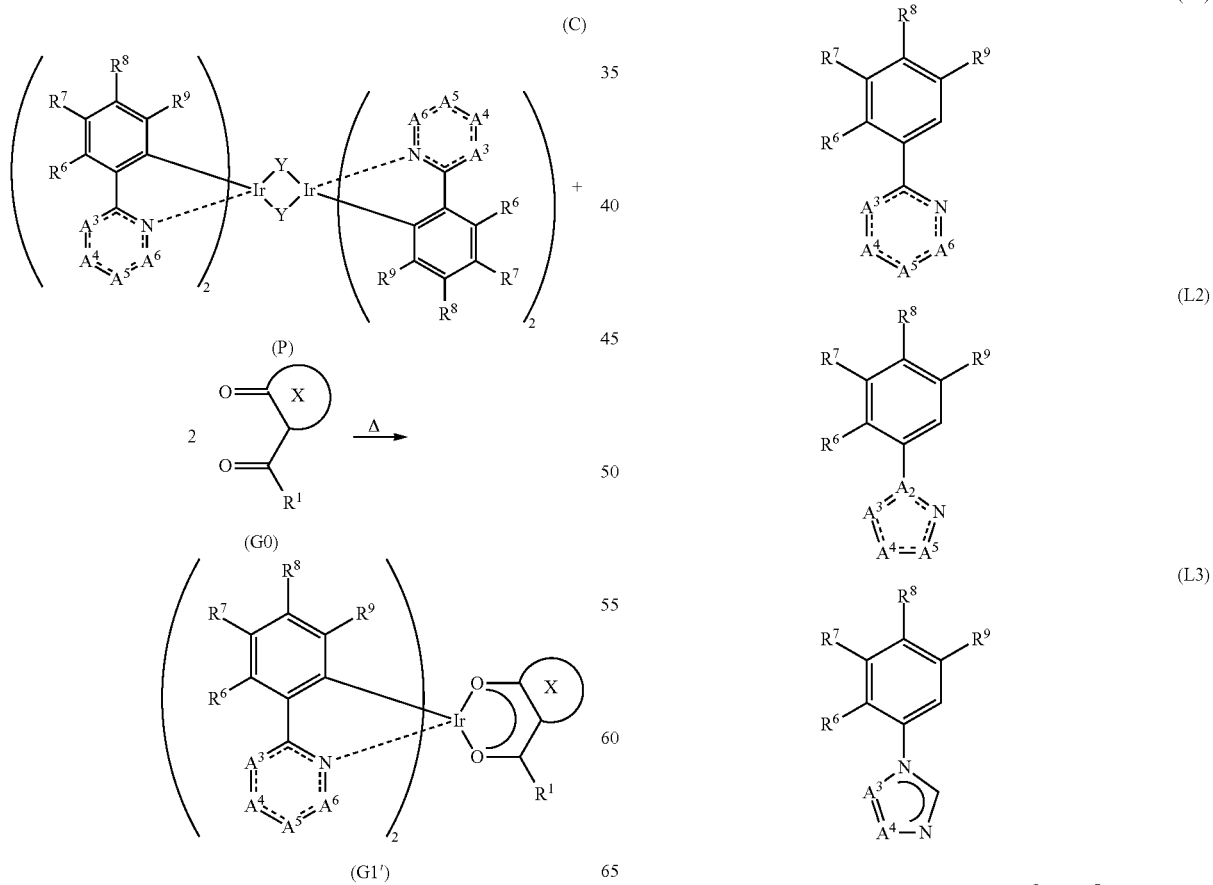

In General Formulae (L1) to (L3), $R^6$ to $R^9$ separately represent hydrogen, a substituted or unsubstituted alkyl group having 1 to 4 carbon atoms, or a substituted or unsubstituted phenyl group. $A^2$ to $A^6$ separately represent oxygen, sulfur, nitrogen, $sp^2$ hybridized nitrogen bonded to any of an alkyl group having 1 to 4 carbon atoms and a phenyl group, $sp^2$ hybridized carbon bonded to hydrogen, or $sp^2$ hybridized carbon bonded to any of an alkyl group having 1 to 4 carbon atoms and a phenyl group. Further, adjacent two atoms of $A^2$ to $A^6$ may be bonded to each other to form a ring.

The above is the description of the example of a method of synthesizing an organometallic complex that is one embodiment of the present invention; however, the present invention is not limited thereto and any other synthesis method may be employed.

The above-described organometallic complex that is one embodiment of the present invention can emit phosphorescence and thus can be used as a light-emitting material or a light-emitting substance of a light-emitting element.

With the use of the organometallic complex that is one embodiment of the present invention, a light-emitting element, a light-emitting device, an electronic device, or a lighting device with high emission efficiency can be obtained. Alternatively, it is possible to obtain a light-emitting element, a light-emitting device, an electronic device, or a lighting device with low power consumption.

The structure described in this embodiment can be combined as appropriate with any of the structures described in the other embodiments.

Embodiment 2

In this embodiment, a light-emitting element in which the organometallic complex described in Embodiment 1 as one embodiment of the present invention is used for a light-emitting layer is described with reference to FIG. 1.

In a light-emitting element described in this embodiment, as illustrated in FIG. 1, an EL layer 102 including a light-emitting layer 113 is provided between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge generation layer (E) 116, and the like in addition to the light-emitting layer 113.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. Thus, the organometallic complex of one embodiment of the present invention functions as a light-emitting substance in the light-emitting element.

The hole-injection layer 111 included in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge generation layer (E) 116 is a layer containing a substance having a high hole-transport property and an acceptor substance. Owing to the acceptor substance, electrons are extracted from the substance having a high hole-transport property and the extracted electrons are injected from the electron-injection layer 115 having an electron-injection property into the light-emitting layer 113 through the electron-transport layer 114.

A specific example in which the light-emitting element described in this embodiment is manufactured is described.

For the first electrode (anode) 101 and the second electrode (cathode) 103, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like.

As the substance having a high hole-transport property which is used for the hole-injection layer 111, the hole-transport layer 112, and the charge generation layer (E) 116, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. In addition, the following carbazole derivatives and the like, can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances mentioned here are mainly ones that have a hole mobility of $10^{-6}$ cm$^2$/Vs or higher. Note that other than these substances, any substance that has a property of transporting more holes than electrons may be used.

Further, a high molecular compound such as poly(N-vinylcarbazole) (abbreviation: PVK); poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

As examples of the acceptor substance that is used for the hole-injection layer 111 and the charge generation layer (E) 116, a transition metal oxide or an oxide of a metal belonging to any of Group 4 to Group 8 of the periodic table can be given. Specifically, molybdenum oxide is particularly preferable.

The light-emitting layer 113 contains the organometallic complex described in Embodiment 1 as a guest material serving as a light-emitting substance and a substance that has higher triplet excitation energy than this organometallic complex as a host material.

Preferable examples of the substance (i.e., host material) used for dispersing any of the above-described organometallic complexes include: any of compounds having an arylamine skeleton, such as 2,3-bis(4-diphenylaminophenyl)quinoxaline (abbreviation: TPAQn) and NPB, carbazole derivatives such as CBP and 4,4',4''-tris(carbazol-9-yl)triphenylamine (abbreviation: TCTA), and metal complexes such as bis[2-(2-hydroxyphenyl)pyridinato]zinc (abbreviation: $Znpp_2$), bis[2-(2-hydroxyphenyl)benzoxazolato]zinc (abbreviation: $Zn(BOX)_2$), bis(2-methyl-8-quinolinolato)(4-phenylphenolato)aluminum (abbreviation: BAlq), and tris(8-quinolinolato)aluminum (abbreviation: $Alq_3$). Alternatively, a high molecular compound such as PVK can be used.

Note that in the case where the light-emitting layer 113 contains the above-described organometallic complex (guest material) and the host material, phosphorescence with high emission efficiency can be obtained from the light-emitting layer 113.

The electron-transport layer 114 is a layer containing a substance having a high electron-transport property. For the electron-transport layer 114, metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2-hydroxyphenyl)benzothiazolato]zinc (abbreviation: $Zn(BTZ)_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly [(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ $cm^2/Vs$ or higher. Note that other than these substances, any substance that has a property of transporting more electrons than holes may be used for the electron-transport layer.

Further, the electron-transport layer 114 is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride ($CaF_2$), or lithium oxide (LiOx), can be used. Alternatively, a rare earth metal compound such as erbium fluoride ($ErF_3$) can be used. Further alternatively, the substances for forming the electron-transport layer 114, which are described above, can be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, alkali metal oxide or alkaline earth metal oxide such as lithium oxide, calcium oxide, barium oxide, and the like can be given. A Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, electron-injection layer 115, and charge generation layer (E) 116 can be formed by a method such as an evaporation method (e.g., a vacuum evaporation method), an ink-jet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the organometallic complex and thus can have higher efficiency than a light-emitting element using a fluorescent compound.

Note that the light-emitting element described in this embodiment is an example of a light-emitting element manufactured using the organometallic complex that is one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Further more, there is also no particular limitation on crystallinity of a semiconductor film used for the TFT. For example, an amorphous semiconductor film, a crystalline semiconductor film, or the like can be given. And also, an oxide semiconductor film, or the like can be used as a material of a semiconductor film used for the TFT.

Note that the structure described in this embodiment can be combined as appropriate with any of the structures described in the other embodiments.

Embodiment 3

In this embodiment, as one embodiment of the present invention, a light-emitting element in which two or more kinds of organic compounds as well as a phosphorescent organometallic iridium complex are used for a light-emitting layer is described.

Figure 2:
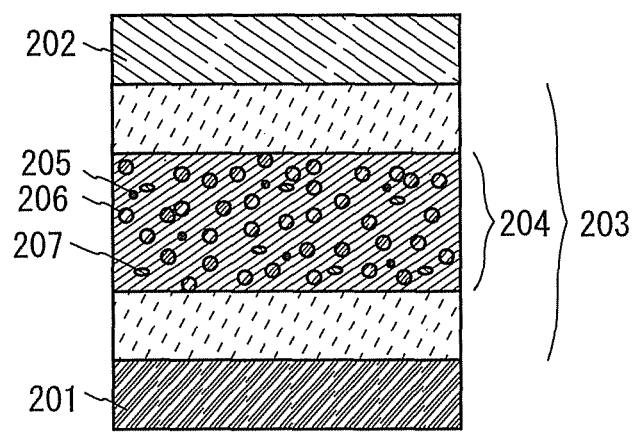
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, a charge generation layer (E), and the like. Note that for the hole-injection layer, the hole-transport layer, the electron-transport layer, the electron-injection layer, and the charge generation layer (E), the substances described in Embodiment 2 can be used.

The light-emitting layer 204 described in this embodiment contains a phosphorescent compound 205 using the phosphorescent organometallic iridium complex described in Embodiment 1, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. The reason for this is that, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency decreases.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound in order to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound and the second organic compound preferably forms an exciplex (also referred to as excited complex). In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound and the second organic compound are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is assumed to occur.

For the phosphorescent compound 205, the phosphorescent organometallic iridium complex described in Embodiment 1 is used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

As examples of a compound which is likely to accept electrons, the following can be given: 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

As examples of a compound which is likely to accept holes, the following can be given: 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenyl-carbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N- phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of the light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

Note that the light-emitting element described in this embodiment is an example of a structure of a light-emitting element; it is possible to apply a light-emitting element having another structure, which is described in another embodiment, to a light-emitting device that is one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, or the like can be given. And also, an oxide semiconductor film, or the like can be used as a material of a semiconductor film used for the TFT.

Note that the structure described in this embodiment can be combined as appropriate with any of the structures described in the other embodiments.

Embodiment 4

In this embodiment, as one embodiment of the present invention, a light-emitting element (hereinafter referred to as tandem light-emitting element) in which a charge generation layer is provided between a plurality of EL layers is described.

Figure 3A:
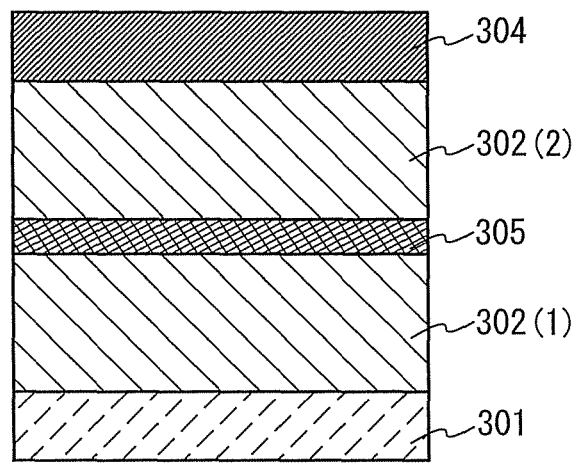
FIGS. 3A and 3B illustrate structures of light-emitting elements.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 2. In addition, although the plurality of EL layers (the first EL layer 302(1) and the second EL layer 302(2)) may have a structure similar to that of the EL layer described in Embodiment 2 or 3, any of the EL layers may have a structure similar to that of the EL layer described in Embodiment 2 or 3. In other words, the structures of the first EL layer 302(1) and the second EL layer 302(2) may be the same or different from each other and can be similar to that of the EL layer described in Embodiment 2 or 3.

Further, a charge generation layer (I) 305 is provided between the plurality of EL layers (the first EL layer 302(1) and the second EL layer 302(2)). The charge generation layer (I) 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge generation layer (I) 305 injects electrons into the first EL layer 302(1) and injects holes into the second EL layer 302(2).

Note that in terms of light extraction efficiency, the charge generation layer (I) 305 preferably has a light-transmitting property with respect to visible light (specifically, the charge generation layer (I) 305 has a visible light transmittance of 40% or more). Further, the charge generation layer (I) 305 functions even if it has lower conductivity than the first electrode 301 or the second electrode 304.

The charge generation layer (I) 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. However, other than the above-described substances, any organic compound that has a property of transporting more holes than electrons may be used.

Further, as the electron acceptor, 7,7,8,8-tetracyano-2,3,5,6-tetrafluoroquinodimethane (abbreviation: F$_4$-TCNQ), chloranil, or the like can be used. Alternatively, a transition metal oxide can be used. Further alternatively, an oxide of metals that belong to Group 4 to Group 8 of the periodic table can be used. Specifically, it is preferable to use vanadium oxide, niobium oxide, tantalum oxide, chromium oxide, molybdenum oxide, tungsten oxide, manganese oxide, or rhenium oxide because the electron-accepting property is high. Among these, molybdenum oxide is especially preferable because it is stable in the air, has a low hygroscopic property, and is easily handled.

On the other hand, in the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, Bphen, BCP, or the like. The substances mentioned here are mainly ones that have an electron mobility of $10^{-6}$ cm$^2$/Vs or higher. Note that other than the above-described substances, any organic compound that has a property of transporting more electrons than holes may be used.

As the electron donor, it is possible to use an alkali metal, an alkaline earth metal, a rare earth metal, a metal belonging to Group 2 or 13 of the periodic table, or an oxide or a carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge generation layer (I) 305 by using any of the above materials can suppress an increase in drive voltage caused by the stack of the EL layers.

Figure 3B:
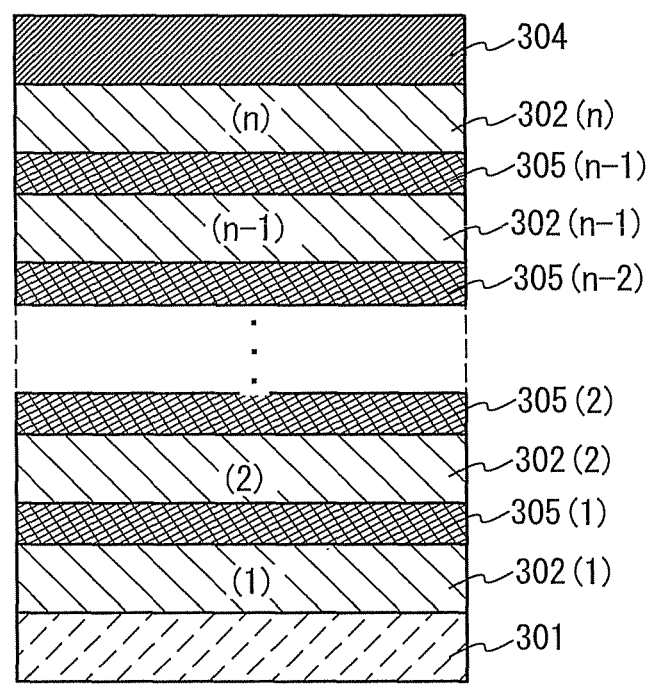

Although this embodiment shows the light-emitting element having two EL layers, the present invention can be similarly applied to a light-emitting element in which n EL layers (302(1) to 302(n)) (n is three or more) are stacked as illustrated in FIG. 3B. In the case where a plurality of EL layers are included between a pair of electrodes as in the light-emitting element according to this embodiment, by provision of charge generation layers (I) (305(1) to 305(n–1)) between the EL layers, light emission in a high luminance region can be obtained with current density kept low. Since the current density can be kept low, the element can have a long lifetime. Further, in application to lighting devices, a voltage drop due to resistance of an electrode material can be reduced and accordingly homogeneous light emission in a large area is possible. Moreover, it is possible to achieve a light-emitting device of low power consumption, which can be driven at a low voltage.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when light obtained from a light-emitting substance and light of a complementary color are mixed, white emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 5

In this embodiment, a light-emitting device which is one embodiment of the present invention is described.

Figure 4:
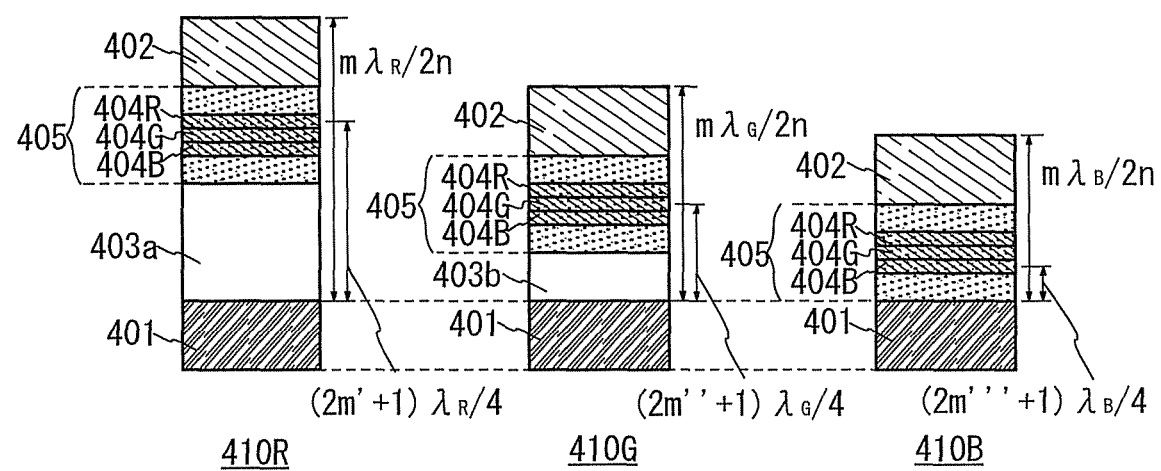
FIG. 4 illustrates a light-emitting device.

A light-emitting device described in this embodiment has a micro optical resonator (microcavity) structure in which a light resonant effect between a pair of electrodes is utilized. The light-emitting device includes, a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least a light-emitting layer 404 serving as a light-emitting region and may further include a hole-injection layer, a hole-transport layer, an electron-transport layer, an electron-injection layer, a charge generation layer (E), and the like. Note that the light-emitting layer 404 contains the phosphorescent organometallic iridium complex that is one embodiment of the present invention.

In this embodiment, a light-emitting device is described which includes light-emitting elements (a first light-emitting element (R) 410R, a second light-emitting element (G) 410G, and a third light-emitting element (B) 410B) having different structures as illustrated in FIG. 4.

The first light-emitting element (R) 410R has a structure in which a first transparent conductive layer 403a; an EL layer 405 including a first light-emitting layer (B) 404B, a second light-emitting layer (G) 404G, and a third light-emitting layer (R) 404R in part; and a semi-transmissive and semi-reflective electrode 402 are sequentially stacked over a reflective electrode 401. The second light-emitting element (G) 410G has a structure in which a second transparent conductive layer 403b, the EL layer 405, and the semi-transmissive and semi-reflective electrode 402 are sequentially stacked over the reflective electrode 401. The third light-emitting element (B) 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element (R) 410R, the second light-emitting element (G) 410G, and the third light-emitting element (B) 410B). The first light-emitting layer (B) 404B emits light ($\lambda_B$) having a peak in a wavelength region from 420 nm to 480 nm. The second light-emitting layer (G) 404G emits light ($\lambda_G$) having a peak in a wavelength region from 500 nm to 550 nm. The third light-emitting layer (R) 404R emits light ($\lambda_R$) having a peak in a wavelength region from 600 nm to 760 nm. Thus, in each of the light-emitting elements (the first light-emitting element (R) 410R, the second light-emitting element (G) 410G, and the third light-emitting element (B) 410B), light emitted from the first light-emitting layer (B) 404B, light emitted from the second light-emitting layer (G) 404G, and light emitted from the third light-emitting layer (R) 404R overlap with each other; accordingly, light having a broad emission spectrum that covers a visible light region can be emitted. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light, emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1 \times 10^{-2}$ Ωcm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1 \times 10^{-2}$ Ωcm or lower is used.

In this embodiment, the thicknesses of the transparent conductive layers (the first transparent conductive layer 403*a* and the second transparent conductive layer 403*b*) provided in the first light-emitting element (R) 410R and the second light-emitting element (G) 410G, respectively, are varied between the light-emitting elements, whereby the light-emitting elements differ in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be enhanced while light with a wavelength that is not resonated therebetween can be attenuated. Thus, when the elements differ in the optical path length from the reflective electrode 401 to the semi-transmissive and semi-reflective electrode 402, light with different wavelengths can be extracted.

Note that the optical path length (also referred to as optical distance) is expressed as a product of an actual distance and a refractive index, and in this embodiment, is a product of an actual thickness and n (refractive index). That is, an optical path length=actual thickness×n.

Further, the total thickness from the reflective electrode 401 to the semi-transmissive and semi-reflective electrode 402 is set to $m\lambda_R/2$ (m is a natural number) in the first light-emitting element (R) 410R; the total thickness from the reflective electrode 401 to the semi-transmissive and semi-reflective electrode 402 is set to $m\lambda_G/2$ (m is a natural number) in the second light-emitting element (G) 410G; and the total thickness from the reflective electrode 401 to the semi-transmissive and semi-reflective electrode 402 is set to $m\lambda_B/2$ (m is a natural number) in the third light-emitting element (B) 410B.

In this manner, the light ($\lambda_R$) emitted from the third light-emitting layer (R) 404R included in the EL layer 405 is mainly extracted from the first light-emitting element (R) 410R, the light ($\lambda_G$) emitted from the second light-emitting layer (G) 404G included in the EL layer 405 is mainly extracted from the second light-emitting element (G) 410G, and the light ($\lambda_B$) emitted from the first light-emitting layer (B) 404B included in the EL layer 405 is mainly extracted from the third light-emitting element (B) 410B. Note that the light extracted from each of the light-emitting elements is emitted from the semi-transmissive and semi-reflective electrode 402 side.

Further, strictly speaking, the total thickness from the reflective electrode 401 to the semi-transmissive and semi-reflective electrode 402 can be the total thickness from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is assumed that the above effect can be sufficiently obtained wherever the reflection regions may be set in the reflective electrode 401 and the semi-transmissive and semi-reflective electrode 402.

Next, in the first light-emitting element (R) 410R, the optical path length from the reflective electrode 401 to the third light-emitting layer (R) 404R is adjusted to a desired thickness ($(2m'+1)\lambda_R/4$, where m' is a natural number); thus, light emitted from the third light-emitting layer (R) 404R can be amplified. Light (first reflected light) that is reflected by the reflective electrode 401 of the light emitted from the third light-emitting layer (R) 404R interferes with light (first incident light) that directly enters the semi-transmissive and semi-reflective electrode 402 from the third light-emitting layer (R) 404R. Therefore, by adjusting the optical path length from the reflective electrode 401 to the third light-emitting layer (R) 404R to the desired value ($(2m'+1)\lambda_R/4$, where m' is a natural number), the phases of the first reflected light and the first incident light can be aligned with each other and the light emitted from the third light-emitting layer (R) 404R can be amplified.

Note that strictly speaking, the optical path length from the reflective electrode 401 to the third light-emitting layer (R) 404R can be the optical path length from a reflection region in the reflective electrode 401 to a light-emitting region in the third light-emit/ting layer (R) 404R. However, it is difficult to precisely determine the positions of the reflection region in the reflective electrode 401 and the light-emitting region in the third light-emitting layer (R) 404R; therefore, it is assumed that the above effect can be sufficiently obtained wherever the reflection region and the light-emitting region may be set in the reflective electrode 401 and the third light-emitting layer (R) 404R, respectively.

Next, in the second light-emitting element (G) 410G, the optical path length from the reflective electrode 401 to the second light-emitting layer (G) 404G is adjusted to a desired thickness ($(2m''+1)\lambda_G/4$, where m'' is a natural number); thus, light emitted from the second light-emitting layer (G) 404G can be amplified. Light (second reflected light) that is reflected by the reflective electrode 401 of the light emitted from the second light-emitting layer (G) 404G interferes with light (second incident light) that directly enters the semi-transmissive and semi-reflective electrode 402 from the second light-emitting layer (G) 404G. Therefore, by adjusting the optical path length from the reflective electrode 401 to the second light-emitting layer (G) 404G to the desired value ($(2m''+1)\lambda_G/4$, where m'' is a natural number), the phases of the second reflected light and the second incident light can be aligned with each other and the light emitted from the second light-emitting layer (G) 404G can be amplified.

Note that strictly speaking, the optical path length from the reflective electrode 401 to the second light-emitting layer (G) 404G can be the optical path length from a reflection region in the reflective electrode 401 to a light-emitting region in the second light-emitting layer (G) 404G. However, it is difficult to precisely determine the positions of the reflection region in the reflective electrode 401 and the light-emitting region in the second light-emitting layer (G) 404G; therefore, it is assumed that the above effect can be sufficiently obtained wherever the reflection region and the light-emitting region may be set in the reflective electrode 401 and the second light-emitting layer (G) 404G, respectively.

Next, in the third light-emitting element (B) 410B, the optical path length from the reflective electrode 401 to the first light-emitting layer (B) 404B is adjusted to a desired thickness $((2m'''+1)\lambda_B/4$, where m''' is a natural number); thus, light emitted from the first light-emitting layer (B) 404B can be amplified. Light (third reflected light) that is reflected by the reflective electrode 401 of the light emitted from the first light-emitting layer (B) 404B interferes with light (third incident light) that directly enters the semi-transmissive and semi-reflective electrode 402 from the first light-emitting layer (B) 404B. Therefore, by adjusting the optical path length from the reflective electrode 401 to the first light-emitting layer (B) 404B to the desired value $((2m'''+1)\lambda_B/4$, where m''' is a natural number), the phases of the third reflected light and the third incident light can be aligned with each other and the light emitted from the first light-emitting layer (B) 404B can be amplified.

Note that strictly speaking, the optical path length from the reflective electrode 401 to the first light-emitting layer (B) 404B in the third light-emitting element can be the optical path length from a reflection region in the reflective electrode 401 to a light-emitting region in the first light-emitting layer (B) 404B. However, it is difficult to precisely determine the positions of the reflection region in the reflective electrode 401 and the light-emitting region in the first light-emitting layer (B) 404B; therefore, it is assumed that the above effect can be sufficiently obtained wherever the reflection region and the light-emitting region may be set in the reflective electrode 401 and the first light-emitting layer (B) 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers and a charge generation layer interposed therebetween are provided in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the emission direction can be increased, whereby power consumption can be reduced. The above structure is particularly useful in the case of being applied to a color display (image display device) including pixels of three or more colors but may also be applied to lighting or the like.

Embodiment 6

In this embodiment, a light-emitting device including a light-emitting element in which the organometallic complex that is one embodiment of the present invention is used for a light-emitting layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 5A and 5B.

Figure 5A:
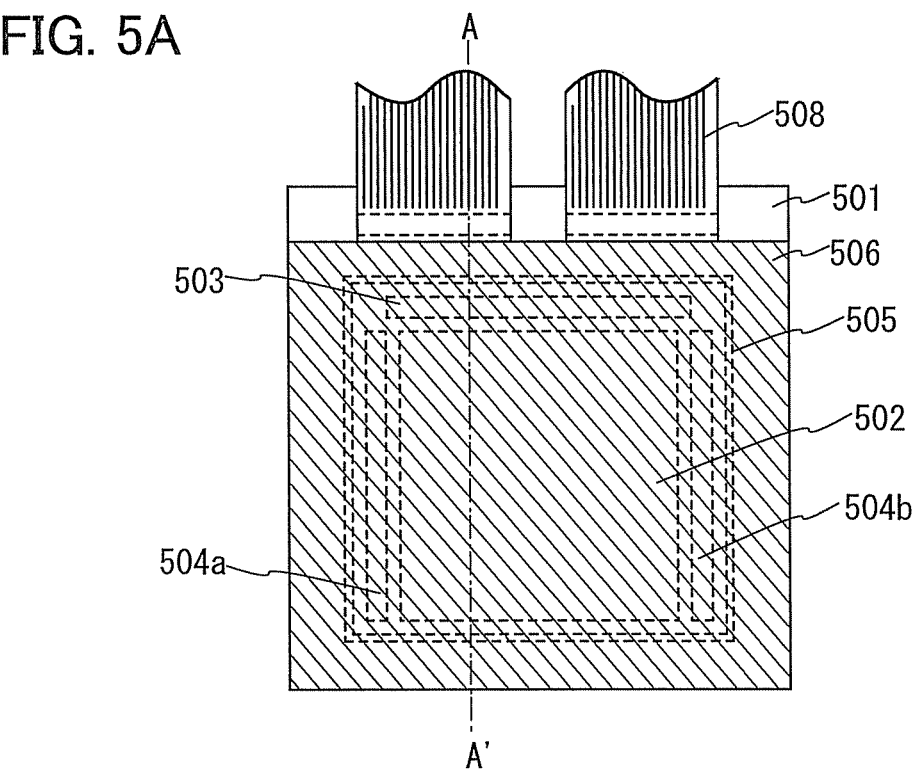
FIGS. 5A and 5B illustrate a light-emitting device.
Figure 5B:
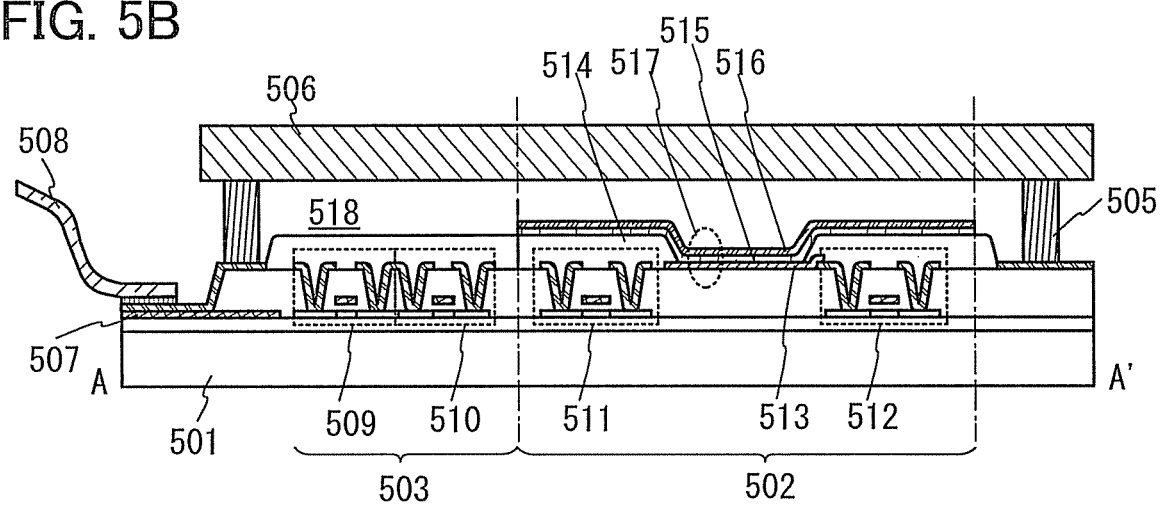

Note that FIG. 5A is a top view illustrating a light-emitting device and FIG. 5B is a cross-sectional view taken along the chain line A-A' in FIG. 5A. The active matrix light-emitting device according to this embodiment includes a pixel portion 502 provided over an element substrate 501, a driver circuit portion (a source line driver circuit) 503, and a driver circuit portion (a gate line driver circuit) 504. The pixel portion 502, the driver circuit portion 503, and the driver circuit portion 504 are sealed between the element substrate 501 and the sealing substrate 506 with a sealant 505.

In addition, a lead wiring 507 is provided over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portion 504. Here is shown an example in which a flexible printed circuit (FPC) 508 is provided as the external input terminal. Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 5B. The driver circuit portion and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and may be formed outside the substrate.

The pixel portion 502 is formed of a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 μm to 3 μm) at the upper end portion. Note that the insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode (cathode) 516 are stacked over the first electrode (anode) 513. In the EL layer 515, at least a light-emitting layer is provided which contains the organometallic complex that is one embodiment of the present invention. Further, in the EL layer 515, a hole-injection layer, a hole-transport layer, an electron-transport layer, an electron-injection layer, a charge generation layer, and the like can be provided as appropriate in addition to the light-emitting layer.

A light-emitting element 517 is formed of a stacked structure of the first electrode (anode) 513, the EL layer 515, and the second electrode (cathode) 516. For the first electrode (anode) 513, the EL layer 515, and the second electrode (cathode) 516, the materials described in Embodiment 2 can be used. Although not illustrated, the second electrode (cathode) 516 is electrically connected to an FPC 508 which is an external input terminal.

Although the cross-sectional view of FIG. 5B illustrates only one light-emitting element 517, a plurality of light-emitting elements are arranged in matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device which is capable of full color display may be fabricated by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), poly (vinyl fluoride) (PVF), polyester, acrylic, or the like can be used.

As described above, an active matrix light-emitting device can be obtained.

Note that the structure described in this embodiment can be combined as appropriate with any of the structures described in the other embodiments.

Embodiment 7

In this embodiment, examples of a variety of electronic devices which are completed using a light-emitting device are described with reference to FIGS. 6A to 6D and FIGS. 7A to 7C. To the light-emitting device, the organometallic complex that is one embodiment of the present invention is applied.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine. Specific examples of these electronic devices are illustrated in FIGS. 6A to 6D.

Figure 6A:
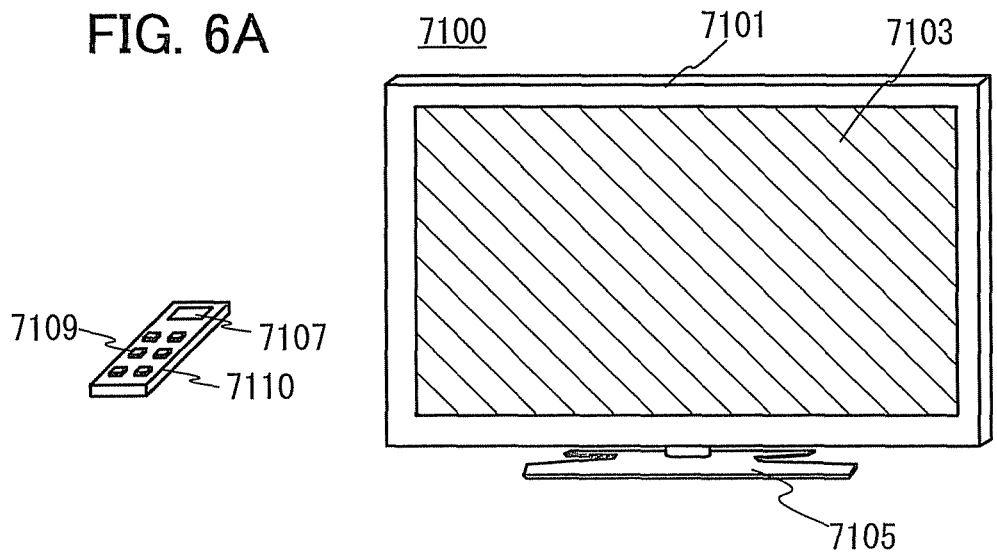
FIGS. 6A to 6D illustrate electronic devices.

FIG. 6A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

Figure 6B:
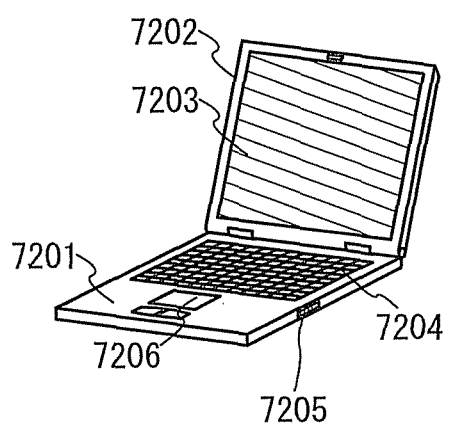

FIG. 6B illustrates a computer having a main body 7201, a housing 7202, a display portion 7203, a keyboard 7204, an external connection port 7205, a pointing device 7206, and the like. Note that this computer is manufactured using the light-emitting device for the display portion 7203.

Figure 6C:
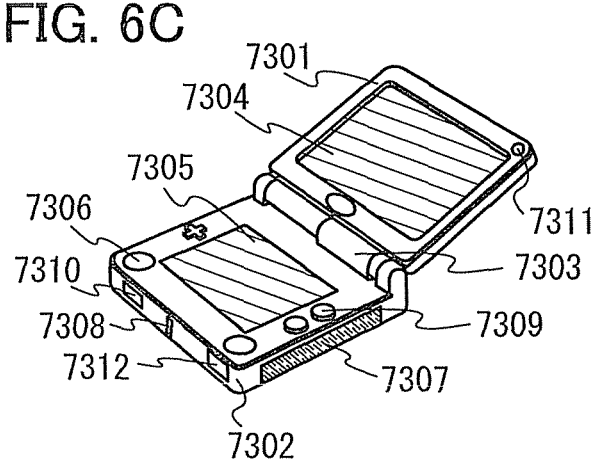

FIG. 6C illustrates a portable game machine having two housings, a housing 7301 and a housing 7302, which are connected with a joint portion 7303 so that the portable game machine can be opened or folded. A display portion 7304 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the light-emitting device is used for at least one of the display portion 7304 and the display portion 7305, and may include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above.

Figure 6D:
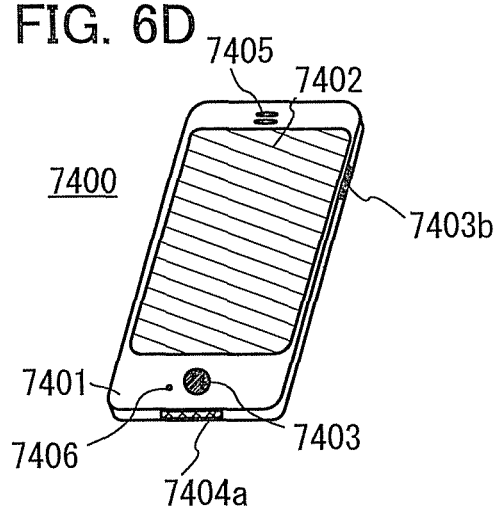

FIG. 6D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using the light-emitting device for the display portion 7402.

When the display portion 7402 of the mobile phone 7400 illustrated in FIG. 6D is touched with a finger or the like, data can be input to the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

Figure 7A:
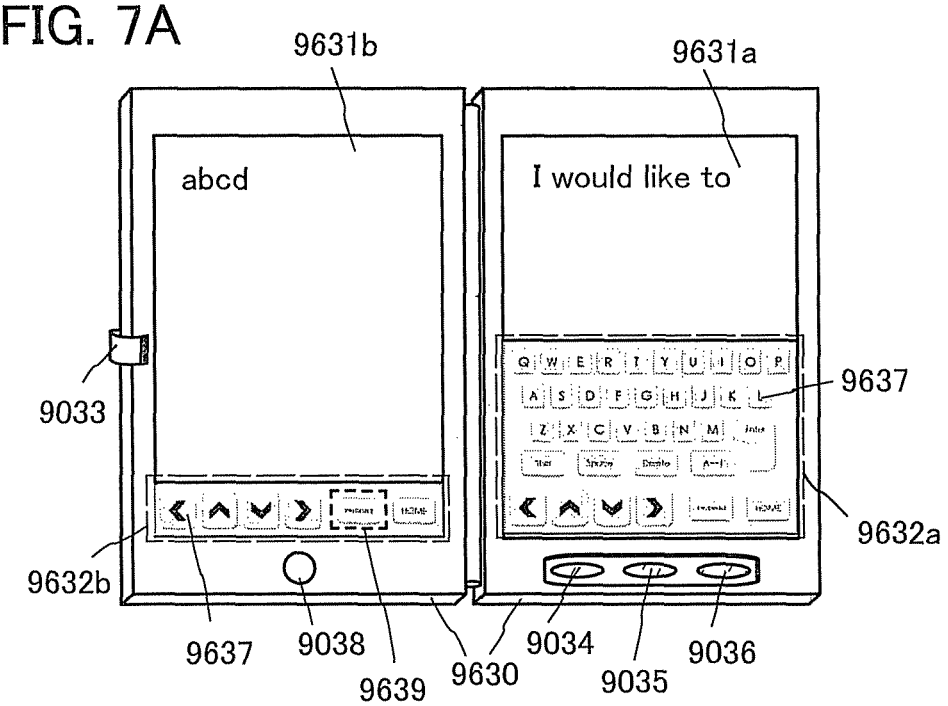
FIGS. 7A to 7C illustrate an electronic device.
Figure 7B:
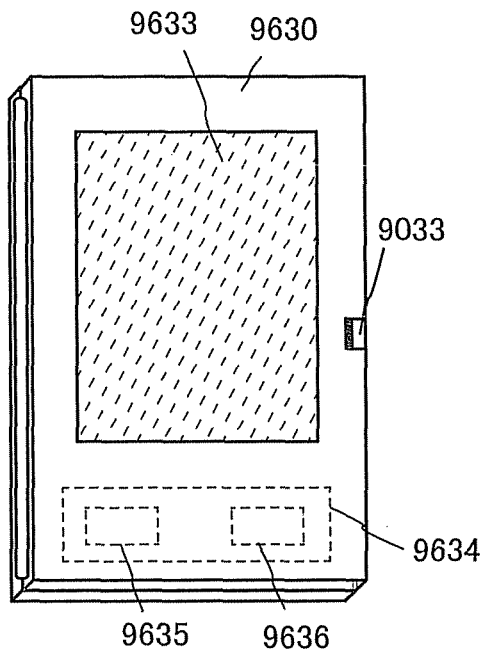

FIGS. 7A and 7B illustrate a foldable tablet terminal. The tablet terminal is opened in FIG. 7A. The tablet terminal includes housings 9630, a display portion 9631a, a display portion 9631b, a display mode switch 9034, a power switch 9035, a power saver switch 9036, a clasp 9033, and an operation switch 9038. The tablet terminal is manufactured using the light-emitting device for either the display portion 9631a or the display portion 9631b or both.

Part of the display portion 9631a can be a touch panel region 9632a and data can be input when a displayed operation key 9637 is touched. Although a structure in which a half region in the display portion 9631a has only a display function and the other half region also has a touch panel function is shown as an example, the display portion 9631a is not limited to the structure. The whole region in the display portion 9631a may have a touch panel function. For example, the display portion 9631a can display keyboard buttons in the whole region to be a touch panel, and the display portion 9631b can be used as a display screen.

As in the display portion 9631a, part of the display portion 9631b can be a touch panel region 9632b. When a keyboard display switching button 9639 displayed on the touch panel is touched with a finger, a stylus, or the like, a keyboard can be displayed on the display portion 9631b.

Touch input can be performed in the touch panel region 9632a and the touch panel region 9632b at the same time.

The display mode switch 9034 can switch the display between portrait mode, landscape mode, and the like, and between monochrome display and color display, for example.

The power saver switch. 9036 can control display luminance in accordance with the amount of external light in use of the tablet terminal detected by an optical sensor incorporated in the tablet terminal. In addition to the optical sensor, another detection device including a sensor for detecting inclination, such as a gyroscope or an acceleration sensor, may be incorporated in the tablet terminal.

Note that FIG. 7A shows an example in which the display portion 9631a and the display portion 9631b have the same display area; however, without limitation thereon, one of the display portions may be different from the other display portion in size and display quality. For example, higher definition images may be displayed on one of the display portions 9631a and 9631b.

The tablet terminal is closed in FIG. 7B. The tablet terminal includes the housings 9630, a solar cell 9633, a charge and discharge control circuit 9634, a battery 9635, and a DCDC converter 9636. In FIG. 7B, a structure including the battery 9635 and the DCDC converter 9636 is illustrated as an example of the charge and discharge control circuit 9634.

Since the tablet terminal is foldable, the housings 9630 can be closed when the tablet terminal is not used. As a result, the display portion 9631a and the display portion 9631b can be protected; thus, a tablet terminal which has excellent durability and excellent reliability in terms of long-term use can be provided.

In addition, the tablet terminal illustrated in FIGS. 7A and 7B can have a function of displaying a variety of kinds of data (e.g., a still image, a moving image, and a text image), a function of displaying a calendar, a date, the time, or the like on the display portion, a touch-input function of operating or editing the data displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 can charge the battery 9635 supplying power to one or both of the housings 9630, which is preferable. The use of a lithium ion battery as the battery 9635 is advantageous in downsizing or the like.

The structure and the operation of the charge and discharge control circuit 9634 illustrated in FIG. 7B will be described with reference to a block diagram in FIG. 7C. The solar cell 9633, the battery 9635, the DCDC converter 9636, a converter 9638, switches SW1 to SW3, and the display portion 9631 are illustrated in FIG. 7C, and the battery 9635, the DCDC converter 9636, the converter 9638, and the switches SW1 to SW3 correspond to the charge and discharge control circuit 9634 illustrated in FIG. 7B.

First, an example of the operation in the case where power is generated by the solar cell 9633 using external light is described. The voltage of power generated by the solar cell is stepped up or down by the DCDC converter 9636 so that the power has a voltage for charging the battery 9635. Then, when the power from the solar cell 9633 is used for the operation of the display portion 9631, the switch SW1 is turned on and the voltage of the power is stepped up or down by the converter 9638 so as to be a voltage needed for the display portion 9631. In addition, when display on the display portion 9631 is not performed, the switch SW1 is turned off and the switch SW2 is turned on so that the battery 9635 may be charged.

Note that the solar cell 9633 is described as an example of a power generation means; however, without limitation thereon, the battery 9635 may be charged using another power generation means such as a piezoelectric element or a thermoelectric conversion element (Peltier element). For example, the battery 9635 may be charged with a non-contact power transmission module which is capable of charging by transmitting and receiving power by wireless (without contact), or another charge means used in combination.

Figure 7C:
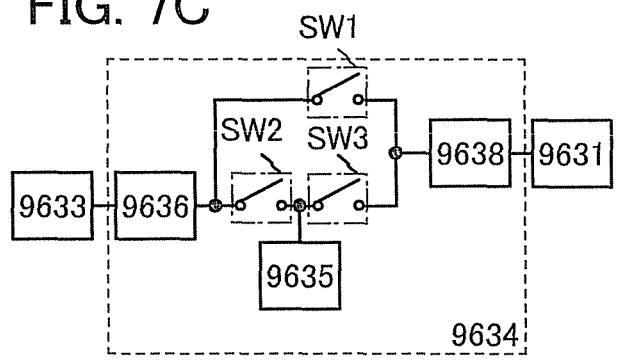

It is needless to say that one embodiment of the present invention is not limited to the electronic device illustrated in FIGS. 7A to 7C as long as the display portion described in this embodiment is included.

As described above, the electronic devices can be obtained by application of the light-emitting device that is one embodiment of the present invention. The light-emitting device has a remarkably wide application range, and can be applied to electronic devices in a variety of fields.

Note that the structure described in this embodiment can be combined as appropriate with any of the structures described in the other embodiments.

Embodiment 8

In this embodiment, examples of a lighting device to which a light-emitting device including the organometallic complex that is one embodiment of the present invention is applied are described with reference to FIG. 8.

Figure 8:
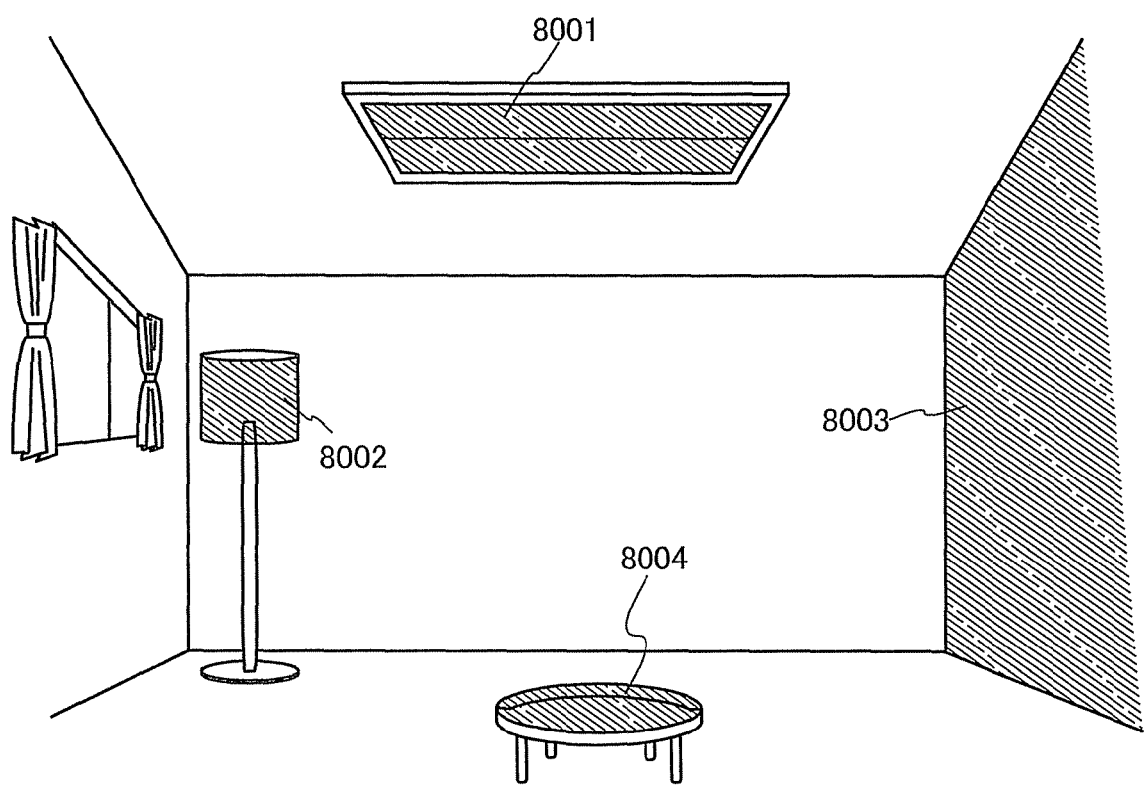
FIG. 8 illustrates lighting devices.

FIG. 8 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

Example 1

Synthesis Example 1

In this example, a synthesis method of [3-(acetyl-κO)-1,7,7-trimethyl-bicyclo[2.2.1]heptan-2-onato-κO]bis[2-(3-methyl-4-pyrimidinyl-κN3)phenyl-κC]iridium(III) (abbreviation: [Ir(mppm)₂(accam)]), the organometallic complex which is one embodiment of the present invention represented by Structural Formula (100) in Embodiment 1, is described. The structure of [Ir(mppm)₂(accam)] is shown below.

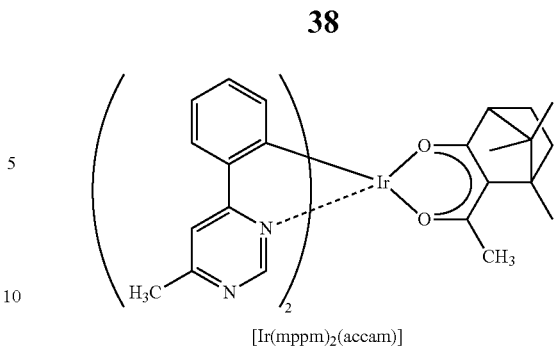

[Ir(mppm)₂(accam)]

Step 1: Synthesis of 3-Acetylcamphor (abbreviation: Haccam)

Into a flask equipped with a reflux pipe was put 1.58 g of sodium hydride, and the air in the flask was replaced with nitrogen. Then, 40 mL of dimethoxyethane (DME) and 5.00 g of (1R)-(+)-camphor were added and this solution was heated and refluxed for 4 hours to cause a reaction. The reacted solution was cooled down to room temperature. With a dropping funnel, 12.4 g of acetyl chloride dissolved in 20 mL of DME was added dropwise in 15 minutes. After that, the solution was heated and refluxed for 3 and a half hours to cause a reaction. The reacted solution was cooled down to room temperature and 10 mL of ethanol was added. This solution was poured into ice water and an organic layer was extracted with ethyl acetate. The obtained organic layer was washed with a 5% sodium carbonate aqueous solution, saturated brine, and water in this order.

This organic layer, 30 mL of a 1 mol/L potassium hydroxide aqueous solution, and 30 mL of methanol were put into a flask, the air in the flask was replaced with nitrogen, and the solution was stirred for 3 hours. The reacted solution was separated into an organic layer and an aqueous layer. The pH of the aqueous layer was adjusted to 2 to 3 by addition of dilute hydrochloric acid. Extraction with ethyl acetate was performed and the solution of the extract was combined with the separated organic layer, washed with water, and dried with magnesium sulfate. The solution after the drying was filtered, and the obtained solution was concentrated and dried. The obtained residue was purified by flash column chromatography (silica gel) using a mixed solvent of hexane and ethyl acetate in a volume ratio of 10:1 as a developing solvent, so that a β-diketone derivative Haccam, the objective substance, was obtained (a pale yellow solution, 12% in yield). The synthesis scheme of Step 1 is shown by (a-1).

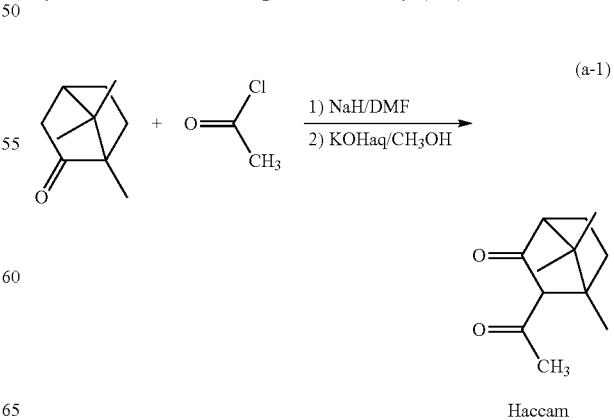

Haccam

Step 2: Synthesis of 3-(Acetyl-κO)-1,7,7-trimethyl-bicyclo[2.2.1]heptan-2-onato-κO]bis[2-(3-methyl-4-pyrimidinyl-κN3)phenyl-κC]iridium(III) (abbreviation: [Ir(mppm)$_2$(accam)])

Further, 25 mL of 2-ethoxyethanol, 1.09 g of di-μ-chloro-tetrakis[2-(3-methyl-4-pyrimidinyl-κN3)phenyl-κC]diiridium(III) (abbreviation: [Ir(mppm)$_2$Cl]$_2$), 0.56 g of Haccam obtained in Step 1, and 1.02 g of sodium carbonate were put into a recovery flask equipped with a reflux pipe, and the reacted solution was bubbled with argon.

Then, irradiation with microwaves (2.45 GHz, 100 W) for 30 minutes was performed to cause a reaction. Dichloromethane was added to the reacted solution and filtration was performed. The solvent of the filtrate was distilled off, and then the obtained residue was purified by flash column chromatography (silica gel) using a mixed solvent of ethyl acetate and dichloromethane in a volume ratio of 1:20 as a developing solvent, to give [Ir(mppm)$_2$(accam)], the organometallic complex according to one embodiment of the present invention, as an orange powder (36% in yield). The synthesis scheme of Step 2 is shown by (a-2).

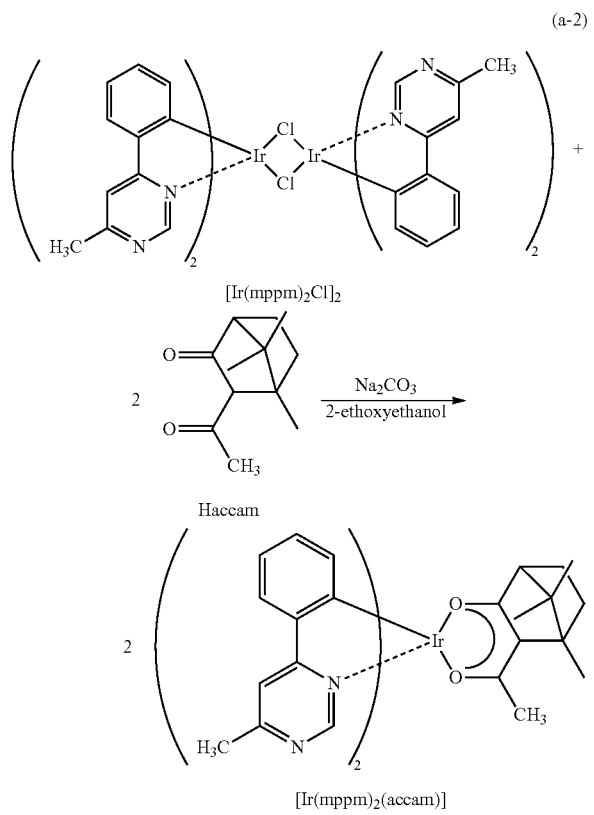

(a-2)

Figure 9:
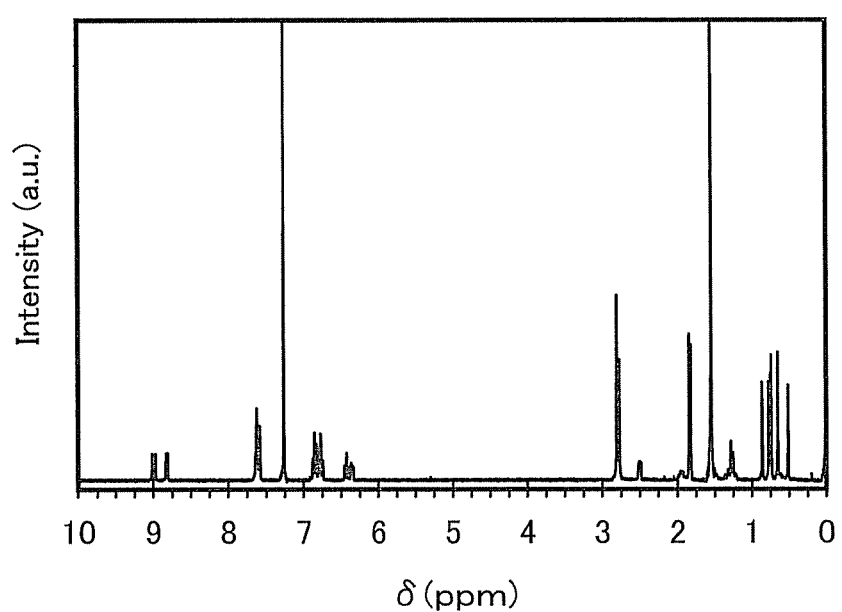
FIG. 9 shows a $^1$H-NMR chart of [Ir(mppm)$_2$(accam)] (abbreviation).

An analysis result by nuclear magnetic resonance ($^1$H-NMR) spectroscopy of the orange powder obtained in Step 2 above is described below. FIG. 9 shows the $^1$H-NMR chart. These results revealed that [Ir(mppm)$_2$(accam)] (abbreviation), the organometallic complex which is one embodiment of the present invention represented by Structural Formula (100), was obtained in Synthesis Example 1.

$^1$H-NMR. δ (CDCl$_3$): 0.52-0.86 (m, 9H), 1.28 (m, 2H), 1.51 (m, 1H), 1.38 (d, 3H), 1.95 (m, 1H), 2.50 (q, 1H), 2.78 (d, 3H), 2.81 (s, 3H), 6.36 (m, 1H), 6.43 (m, 1H), 6.77 (m, 2H), 6.85 (m, 2H), 7.62 (m, 4H), 8.82 (d, 1H), 8.99 (d, 1H).

Figure 10:
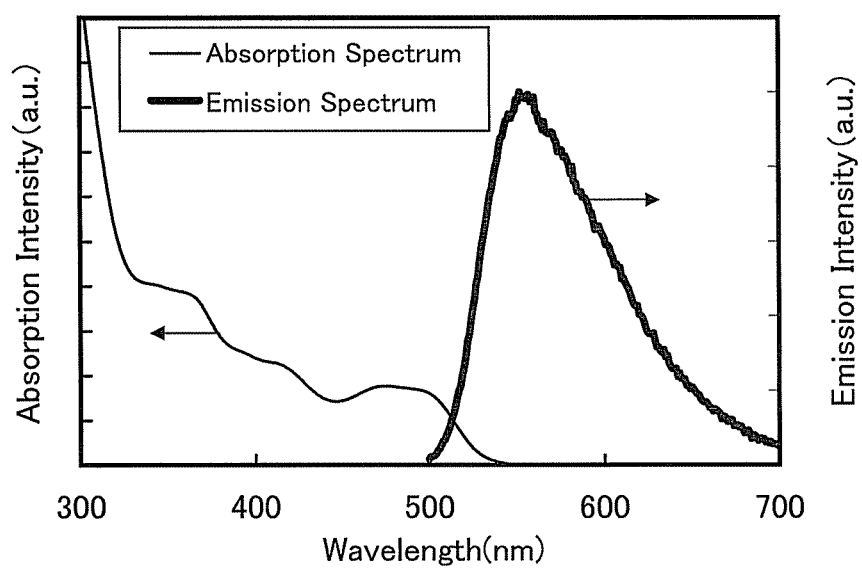
FIG. 10 shows an ultraviolet-visible absorption spectrum and an emission spectrum of [Ir(mppm)$_2$(accam)] (abbreviation).

Next, an ultraviolet-visible absorption spectrum (hereinafter, simply referred to as an "absorption spectrum") of a dichloromethane solution of [Ir(mppm)$_2$(accam)] (abbreviation) and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution (0.115 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed dichloromethane solution (0.115 mmol/L) was put in a quartz cell. Measurement results of the obtained absorption and emission spectra are shown in FIG. 10, in which the horizontal axis represents wavelength and the vertical axes represent absorption intensity and emission intensity. In FIG. 10 where there are two solid lines, the thin line represents the absorption spectrum and the thick line represents the emission spectrum. Note that the absorption spectrum in FIG. 10 is the results obtained in such a way that the absorption spectrum measured by putting only dichloromethane in a quartz cell was subtracted from the absorption spectrum measured by putting the dichloromethane solution (0.115 mmol/L) in a quartz cell.

As shown in FIG. 10, [Ir(mppm)$_2$(accam)] (abbreviation), the organometallic complex that is one embodiment of the present invention, has an emission peak at 553 nm, and yellow green light emission was observed from the dichloromethane solution.

Next, the absolute quantum yield of [Ir(mppm)$_2$(accam)] (abbreviation) which is represented by Structural Formula (100) and was obtained in this example was measured. The measurement of the absolute quantum yield was conducted using an absolute quantum yield measurement system C9920-02, manufactured by Hamamatsu Photonics K. K. The form of a sample was a toluene solution (1×10$^{-5}$ mol/L). The measurement results showed that the quantum yield of [Ir(mppm)$_2$(accam)] (abbreviation), the organometallic complex that is one embodiment of the present invention, is 79%. On the other hand, the absolute quantum yield of a compound represented by Structural Formula (R01), which was subjected to the measurement under similar conditions as a comparative example, was 77%. The above results revealed that emission efficiency is higher with the β-diketone having a cyclic structure than with a structure not having a cyclic structure, such as acetylacetone.

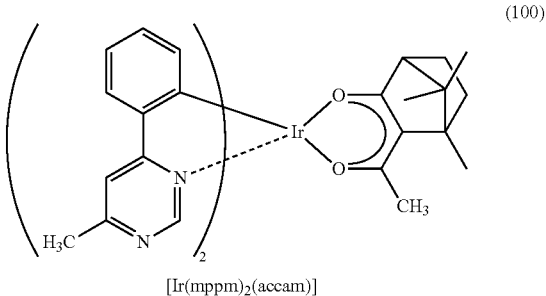

(100)

[Ir(mppm)$_2$(accam)]

-continued

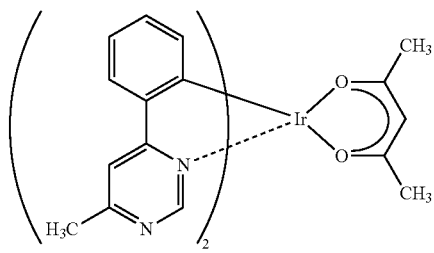

(R01)

Example 2

Synthesis Example 2

In this example, a synthesis method of [2-(acetyl-κO)-cyclohexanonato-κO]bis[2-(3-methyl-4-pyrimidinyl-κN3)phenyl-κC]iridium(III) (abbreviation: [Ir(mppm)$_2$(achex)]), the organometallic complex which is one embodiment of the present invention represented by Structural Formula (101) in Embodiment 1, is described. The structure of [Ir(mppm)$_2$(achex)] is shown below.

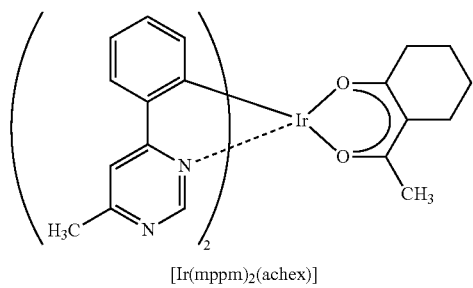

[Ir(mppm)$_2$(achex)]

Synthesis of [2-(Acetyl-κO)-cyclohexanonato-κO]bis[2-(3-methyl-4-pyrimidinyl-κN3)phenyl-κC]iridium(III) (abbreviation: [Ir(mppm)$_2$(achex)])

First, 25 mL of 2-ethoxyethanol, 0.93 g of di-μ-chloro-tetrakis[2-(3-methyl-4-pyrimidinyl-κN3)phenyl-κC]diiridium(III) (abbreviation: [Ir(mppm)$_2$Cl]$_2$), 0.35 g of 2-acetylcyclohexanone (abbreviation: Hachex), and 0.87 g of sodium carbonate were put into a recovery flask equipped with a reflux pipe, and the reacted solution was bubbled with argon. Then, irradiation with microwaves (2.45 GHz, 100 W) for 30 minutes was performed to cause a reaction. The reacted solution was filtered and the residue was washed with methanol, water, ethanol, and methanol in this order. The obtained residue was purified by flash column chromatography (silica gel) using a mixed solvent of ethyl acetate and dichloromethane in a volume ratio of 1:9 as a developing solvent, to give [Ir(mppm)$_2$(achex)], the organometallic complex according to one embodiment of the present invention, as an orange powder (11% in yield). The synthesis scheme is shown by (b-1).

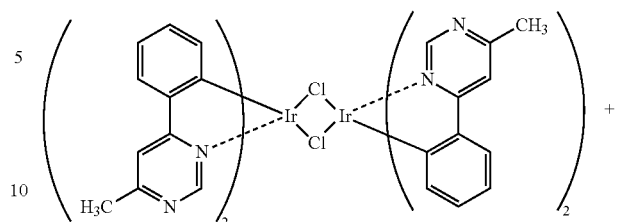

Figure 11:
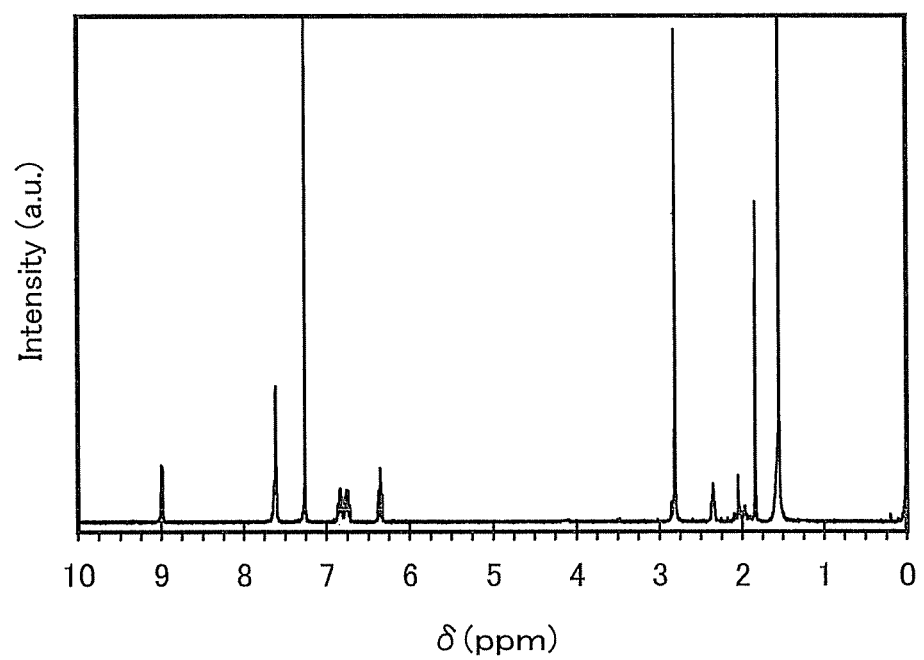
FIG. 11 shows a $^1$H-NMR chart of [Ir(mppm)$_2$(achex)] (abbreviation).

An analysis result by nuclear magnetic resonance ($^1$H-NMR) spectroscopy of the orange powder obtained by the above synthesis method is described below. FIG. 11 shows the $^1$H-NMR chart. These results revealed that [Ir(mppm)$_2$(achex)] (abbreviation), the organometallic complex which is one embodiment of the present invention represented by Structural Formula (101), was obtained in Synthesis Example 2.

$^1$H-NMR. δ (CDCl$_3$): 1.55 (m, 4H), 1.84 (s, 3H), 1.97 (m, 1H), 2.05 (m, 1H), 2.35 (m, 2H), 2.81 (s, 6H), 6.36 (t, 2H), 6.75 (ddt, 2H), 6.84 (ddt, 2H), 7.62 (m, 4H), 8.99 (d, 2H).

Figure 12:
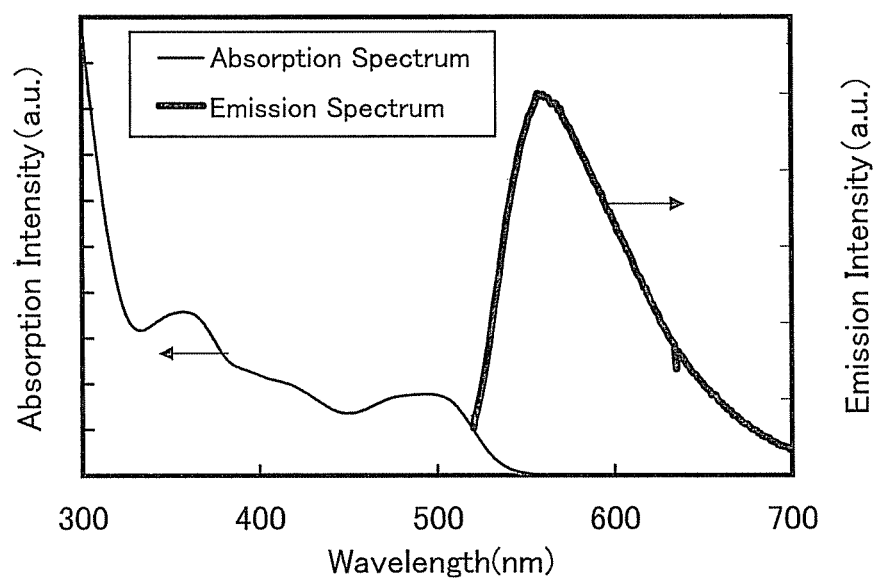
FIG. 12 shows an ultraviolet-visible absorption spectrum and an emission spectrum of [Ir(mppm)$_2$(achex)] (abbreviation).

Next, an ultraviolet-visible absorption spectrum (hereinafter, simply referred to as an "absorption spectrum") of a dichloromethane solution of [Ir(mppm)$_2$(achex)] (abbreviation) and an emission spectrum thereof were measured. The measurement of the absorption spectrum was conducted at room temperature, for which an ultraviolet-visible light spectrophotometer (V550 type manufactured by Japan. Spectroscopy Corporation) was used and the dichloromethane solution (0.114 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed dichloromethane solution (0.114 mmol/L) was put in a quartz cell. Measurement results of the obtained absorption and emission spectra are shown in FIG. 12, in which the horizontal axis represents wavelength and the vertical axes represent absorption intensity and emission intensity. In FIG. 12 where there are two solid lines, the thin line represents the absorption spectrum and the thick line represents the emission spectrum. Note that the absorption spectrum in FIG. 12 is the results obtained in such a way that the absorption spectrum measured by putting only dichloromethane in a quartz cell was subtracted from the absorption spectrum measured by putting the dichloromethane solution (0.114 mmol/L) in a quartz cell.

As shown in FIG. 12, [Ir(mppm)$_2$(achex)] (abbreviation), the organometallic complex that is one embodiment of the present invention, has an emission peak at 560 nm, and yellow green light emission was observed from the dichloromethane solution.

Next, the absolute quantum yield of [Ir(mppm)$_2$(achex)] (abbreviation) which is represented by Structural Formula (101) and was obtained in this example was measured. The measurement of the absolute quantum yield was conducted using an absolute quantum yield measurement system C9920-02, manufactured by Hamamatsu Photonics K. K. The form of a sample was a toluene solution ($1\times10^{-5}$ mol/L). The measurement results showed that the quantum yield of [Ir(mppm)$_2$(achex)] (abbreviation), the organometallic complex which is one embodiment of the present invention, is 83%. The above results revealed that emission efficiency is higher with the β-diketone having a cyclic structure than with a structure not having a cyclic structure, such as acetylacetone.

Example 3

Synthesis Example 3

In this example, a synthesis method of [2-(acetyl-κO)-cyclopentanonato-κO]bis[2-(6-methyl-4-pyrimidinyl-κN3)phenyl-κC]iridium(III) (abbreviation: [Ir(mppm)$_2$(acpen)]), the organometallic complex which is one embodiment of the present invention represented by Structural Formula (104) in Embodiment 1, is described. The structure of [Ir(mppm)$_2$(acpen)] is shown below.

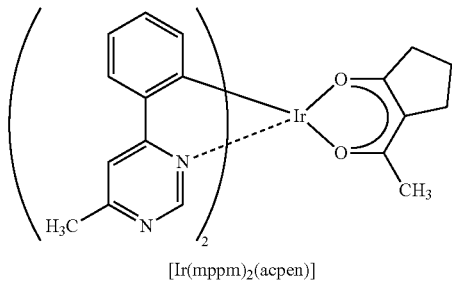

[Ir(mppm)$_2$(acpen)]

Step 2: Synthesis of [2-(Acetyl-κO)-cyclopentanonato-κO]bis[2-(6-methyl-4-pyrimidinyl-κN3)phenyl-κC]iridium(III) (abbreviation: [Ir(mppm)$_2$(acpen)])

First, 25 mL of 2-ethoxyethanol, 0.95 g of di-β-chloro-tetrakis[2-(3-methyl-4-pyrimidinyl-κN3)phenyl-κC]diiridium(III) (abbreviation: [Ir(mppm)$_2$Cl]$_2$), 0.32 g of 2-acetyl-cyclopentanone (abbreviation: Hacpen), and 0.89 g of sodium carbonate were put into a recovery flask equipped with a reflux pipe, and the reacted solution was bubbled with argon. Then, irradiation with microwaves (2.45 GHz, 100 W) for 30 minutes was performed to cause a reaction. The reacted solution was filtered and the residue was washed with methanol, water, and methanol in this order. The obtained residue was purified by flash column chromatography (silica gel) using a mixed solvent of ethyl acetate and dichloromethane in a volume ratio of 1:9 as a developing solvent, to give [Ir(mppm)$_2$(acpen)] (abbreviation), the organometallic complex according to one embodiment of the present invention, as an orange powder (23% in yield). The synthesis scheme is shown by (c-1).

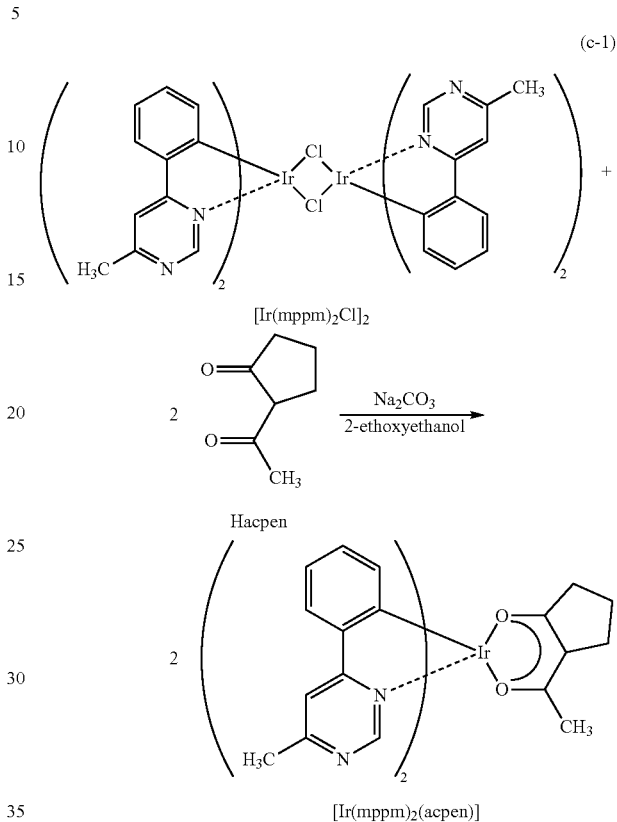

Figure 13:
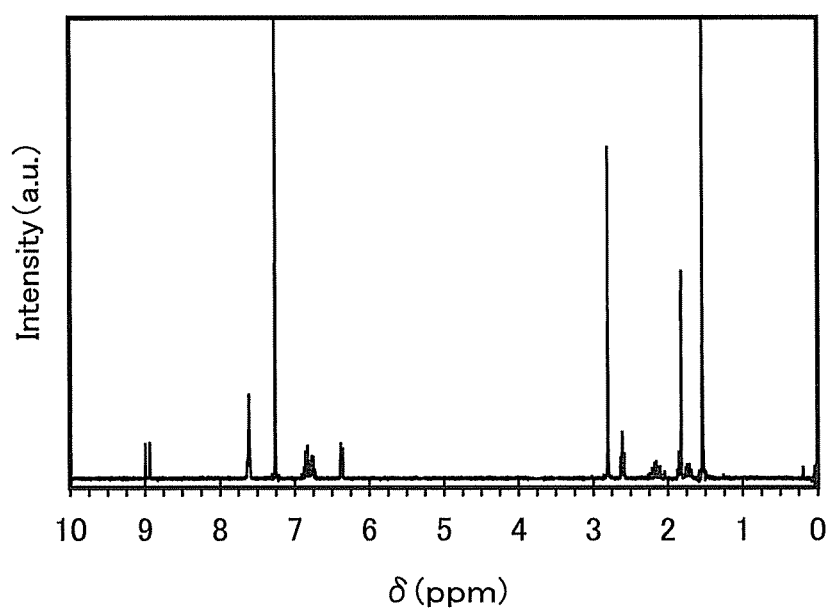
FIG. 13 shows a $^1$H-NMR chart of [Ir(mppm)$_2$(acpen)] (abbreviation).

An analysis result by nuclear magnetic resonance ($^1$H-NMR) spectroscopy of the orange powder obtained by the above synthesis method is described below. FIG. 13 shows the $^1$H-NMR chart. These results revealed that [Ir(mppm)$_2$(acpen)] (abbreviation), the organometallic complex which is one embodiment of the present invention represented by Structural Formula (104), was obtained in Synthesis Example 3.

$^1$H-NMR. δ (CDCl$_3$): 1.73 (m, 2H), 1.82 (s, 3H), 2.15 (m, 2H), 2.64 (t, 2H), 2.81 (s, 6H), 6.34 (d, 2H), 6.75-6.88 (m, 4H), 7.61 (m, 4H), 8.97 (d, 2H).

Figure 14:
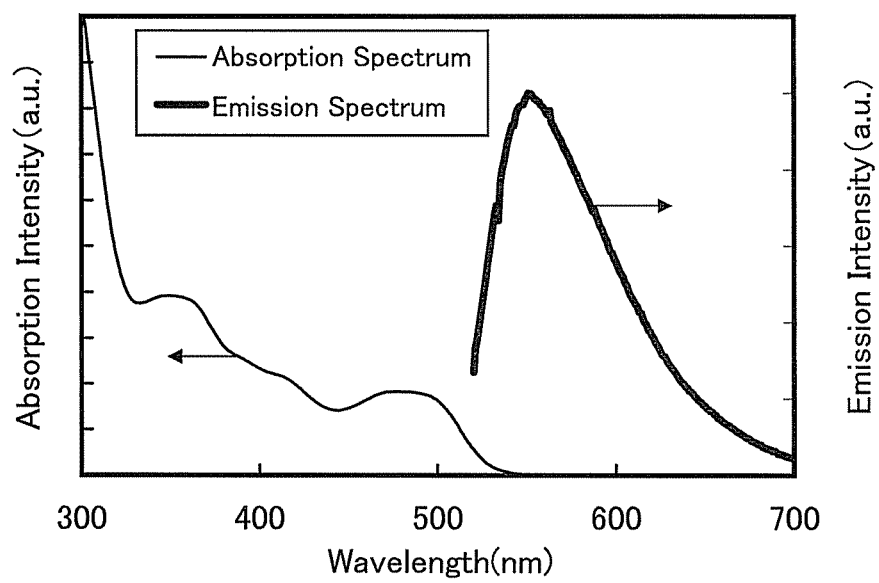
FIG. 14 shows an ultraviolet-visible absorption spectrum and an emission spectrum of [Ir(mppm)$_2$(acpen)] (abbreviation).

Next, an ultraviolet-visible absorption spectrum (hereinafter, simply referred to as an "absorption spectrum") of a dichloromethane solution of [Ir(mppm)$_2$(acpen)] (abbreviation) and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution (0.132 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed dichloromethane solution (0.132 mmol/L) was put in a quartz cell. Measurement results of the obtained absorption and emission spectra are shown in FIG. 14, in which the horizontal axis represents wavelength and the vertical axes represent absorption intensity and emission intensity. In FIG. 14 where there are two solid lines, the thin line represents the absorption spectrum and the thick line represents the emission spectrum. Note that the absorption spectrum in FIG. 14 is the results obtained in such a way that the absorption spectrum measured by putting only dichloromethane in a quartz cell was subtracted from the absorption spectrum measured by putting the dichloromethane solution (0.132 mmol/L) in a quartz cell.

As shown in FIG. 14, [Ir(mppm)$_2$(acpen)] (abbreviation), the organometallic complex that is one embodiment of the present invention, has an emission peak at 552 nm, and yellow green light emission was observed from the dichloromethane solution.

Next, the absolute quantum yield of [Ir(mppm)$_2$(acpen)] (abbreviation) which is represented by Structural Formula (104) and was obtained in this example was measured. The measurement of the absolute quantum yield was conducted using an absolute quantum yield measurement system C9920-02, manufactured by Hamamatsu Photonics K. K. The form of a sample was a toluene solution (1×10$^{-5}$ mol/L). The measurement results showed that the quantum yield of [Ir(mppm)$_2$(acpen)] (abbreviation), the organometallic complex which is one embodiment of the present invention, is 89%. The above results revealed that emission efficiency is higher with the β-diketone having a cyclic structure than with a structure not having a cyclic structure, such as acetylacetone.

Example 4

Synthesis Example 4

In this example, a synthesis method of [2-(acetyl-κO)-cyclohexanonato-κO]bis[2-(3,5-diphenyl-2-pyrazinyl-κN)phenyl-κC]iridium(III) (abbreviation: [Ir(tppr)$_2$(achex)]), the organometallic complex which is one embodiment of the present invention represented by Structural Formula (113) in Embodiment 1, is described. The structure of [Ir(tppr)$_2$(achex)] is shown below.

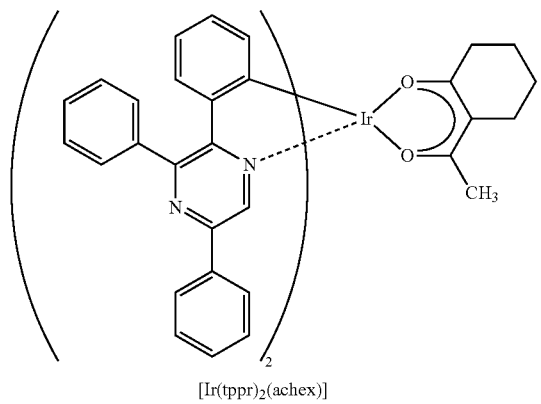

[Ir(tppr)$_2$(achex)]

Synthesis of [2-(Acetyl-κO)-cyclohexanonato-κO]bis[2-(3,5-diphenyl-2-pyrazinyl-κN)phenyl-κC]iridium(III) (abbreviation: [Ir(tppr)$_2$(achex)])

First, 25 mL of 2-ethoxyethanol, 0.42 g of di-μ-chloro-tetrakis[2-(3,5-diphenyl-2-pyrazinyl-κN)phenyl-κC]diiridium(III) (abbreviation: [Ir(tppr)$_2$Cl]$_2$), 0.27 g of 2-acetylcyclohexanone (abbreviation: Hachex), and 0.26 g of sodium carbonate were put into a recovery flask equipped with a reflux pipe, and the reacted solution was bubbled with argon. Then, irradiation with microwaves (2.45 GHz, 100 W) for 30 minutes was performed to cause a reaction. The reacted solution was concentrated and dried. The obtained residue was washed with ethanol and hexane in this order, and was purified by flash column chromatography (silica gel) using a mixed solvent of hexane and dichloromethane in a volume ratio of 1:4 as a developing solvent, to give [Ir(tppr)$_2$(achex)], the organometallic complex according to one embodiment of the present invention, as a red powder (16% in yield). The synthesis scheme is shown by (d-1).

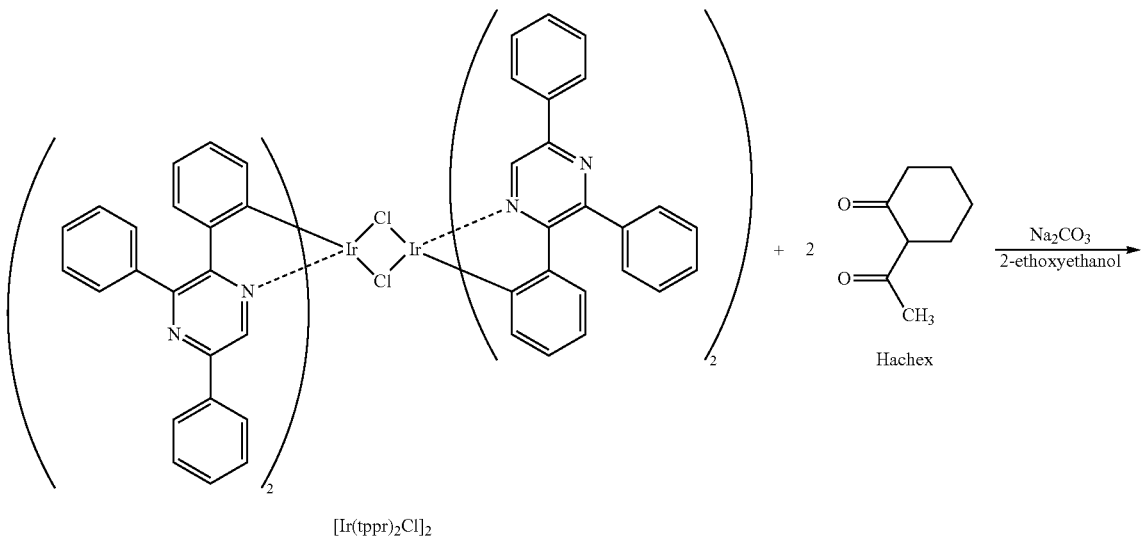

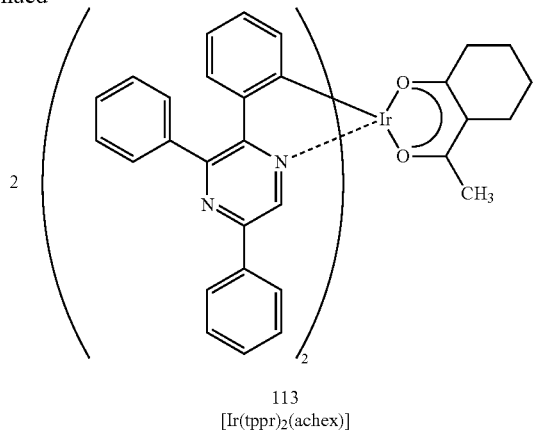

113
[Ir(tppr)₂(achex)]

Figure 15:
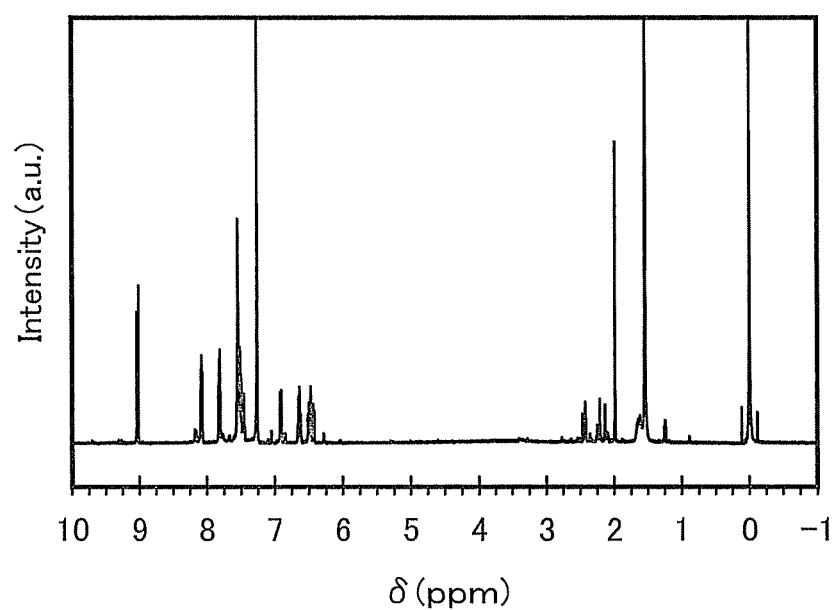
FIG. 15 shows a $^1$H-NMR chart of [Ir(tppr)$_2$(achex)] (abbreviation).

An analysis result by nuclear magnetic resonance (¹H-NMR) spectroscopy of the red powder obtained by the above synthesis method is described below. FIG. 15 shows the ¹H-NMR chart. These results revealed that [Ir(tppr)₂(achex)] (abbreviation), the organometallic complex which is one embodiment of the present invention represented by Structural Formula (113), was obtained in Synthesis Example 4.

¹H-NMR. δ (CDCl₃): 1.61 (m, 4H), 1.99 (s, 3H), 2.14 (m, 1H), 2.21 (m, 1H), 2.43 (m, 2H), 6.48 (m, 4H), 6.64 (m, 2H), 6.90 (d, 2H), 7.55 (m, 12H), 7.81 (m, 4H), 8.08 (m, 4H), 9.03 (d, 2H).

Figure 16:
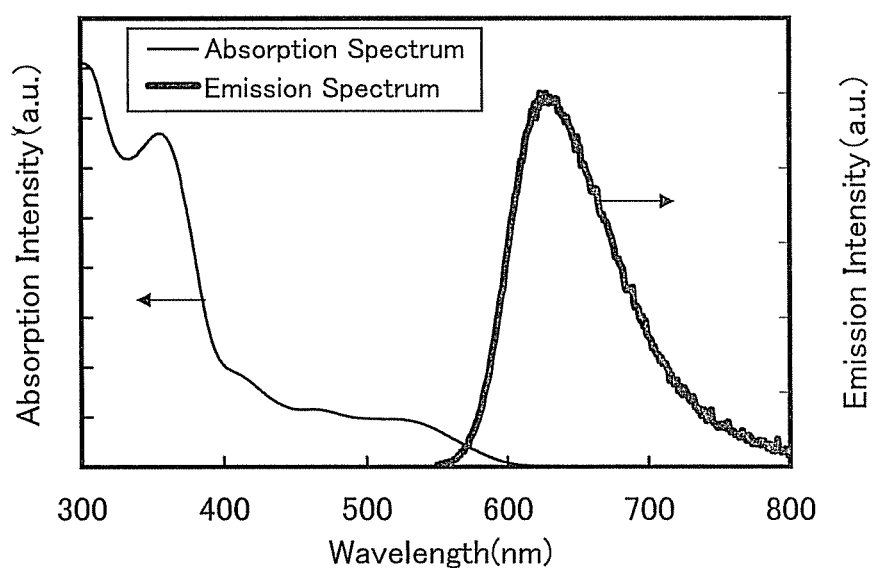
FIG. 16 shows an ultraviolet-visible absorption spectrum and an emission spectrum of [Ir(tppr)$_2$(achex)] (abbreviation).

Next, an ultraviolet-visible absorption spectrum (hereinafter, simply referred to as an "absorption spectrum") of a dichloromethane solution of [Ir(tppr)₂(achex)] (abbreviation) and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution (0.0824 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed dichloromethane solution (0.0824 mmol/L) was put in a quartz cell. Measurement results of the obtained absorption and emission spectra are shown in FIG. 16, in which the horizontal axis represents wavelength and the vertical axes represent absorption intensity and emission intensity. In FIG. 16 where there are two solid lines, the thin line represents the absorption spectrum and the thick line represents the emission spectrum. Note that the absorption spectrum in FIG. 16 is the results obtained in such a way that the absorption spectrum measured by putting only dichloromethane in a quartz cell was subtracted from the absorption spectrum measured by putting the dichloromethane solution (0.0824 mmol/L) in a quartz cell.

As shown in FIG. 16, [Ir(tppr)₂(achex)] (abbreviation), the organometallic complex that is one embodiment of the present invention, has an emission peak at 625 nm, and red light emission was observed from the dichloromethane solution.

Example 5

Figure 17:
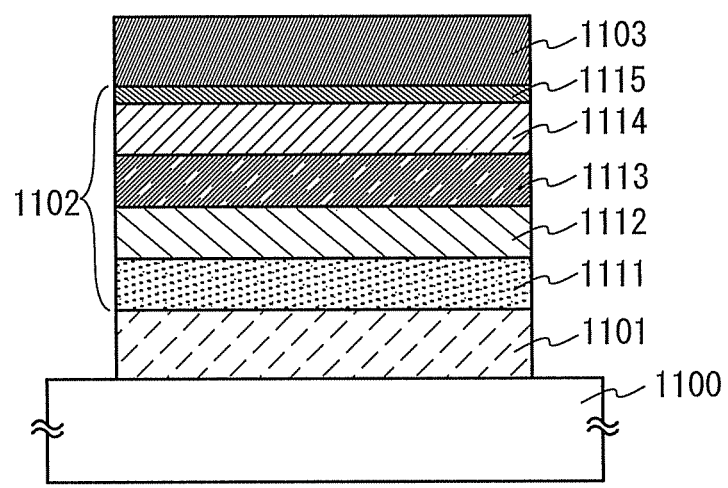
FIG. 17 illustrates a light-emitting element.

In this example, a light-emitting element 1 in which [Ir(mppm)₂(accam)] (abbreviation), the phosphorescent organometallic iridium complex represented by Structural Formula (100), is used for a light-emitting layer is described with reference to FIG. 17. Chemical formulae of materials used in this example are shown below.

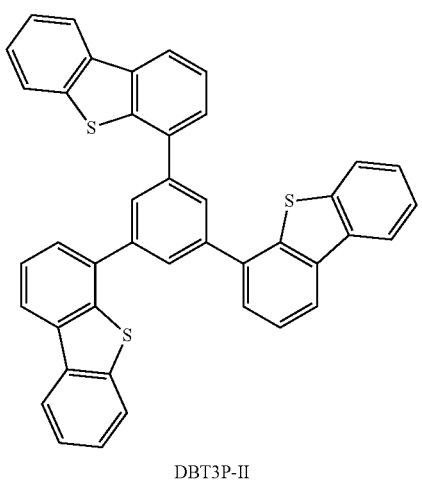

DBT3P-II

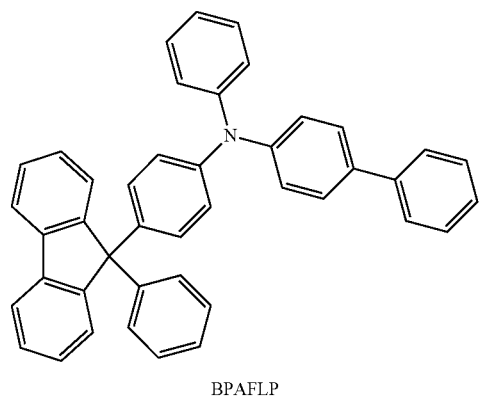

BPAFLP

-continued

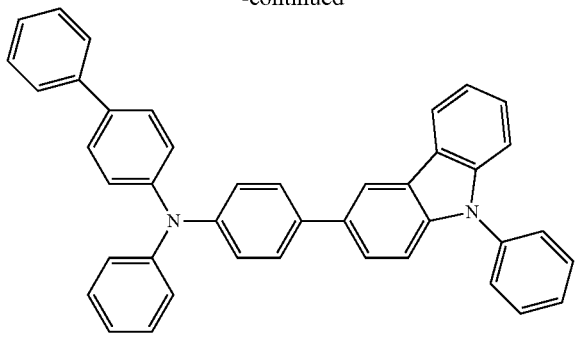

PCBA1BP

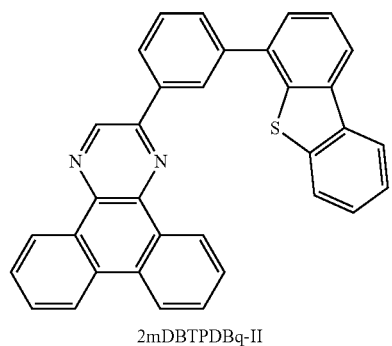

2mDBTPDBq-II

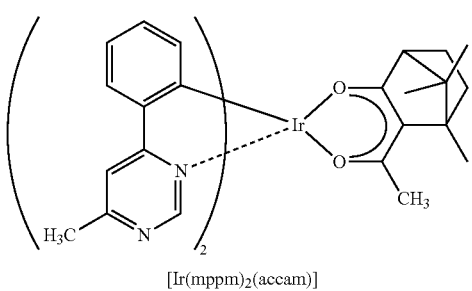

[Ir(mppm)₂(accam)]

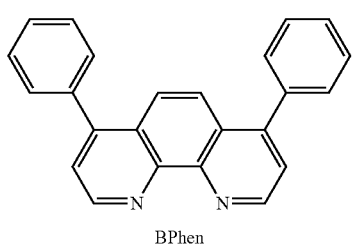

BPhen

《 Fabrication of Light-Emitting Element 1》

First, indium tin oxide containing silicon oxide (ITSO) was deposited over a glass substrate 1100 by a sputtering method, so that a first electrode 1101 which functions as an anode was formed. The thickness was 110 nm and the electrode area was 2 mm×2 mm.

Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were co-evaporated with a mass ratio of DBT3P-II (abbreviation) to molybdenum oxide being 4:2, whereby the hole-injection layer 1111 was formed over the first electrode 1101. The thickness of the hole-injection layer 1111 was 40 nm. Note that the co-evaporation is an evaporation method in which some different substances are evaporated from some different evaporation sources at the same time.

Then, 4-phenyl-4'-(9-phenylfluoren-9-yl)triphenylamine (abbreviation: BPAFLP) was deposited by evaporation to a thickness of 20 nm, so that the hole-transport layer 1112 was formed.

Next, the light-emitting layer 1113 was formed over the hole-transport layer 1112 in the following manner. Co-evaporated were 2-[3-(dibenzothiophen-4-yl)phenyl]dibenzo[f,h]quinoxaline (abbreviation: 2mDBTPDBq-II), 4-phenyl-4'-(9-phenyl-9H-carbazol-3-yl)triphenylamine (abbreviation: PCBA1BP), and [3-(acetyl-κO)-1,7,7-trimethyl-bicyclo[2.2.1]heptan-2-onato-κO]bis[2-(3-methyl-4-pyrimidinyl-κN3)phenyl-κC]iridium(III) (abbreviation: [Ir(mppm)₂(accam)]) with a mass ratio of 2mDBTPDBq-II (abbreviation) to PCBA1BP (abbreviation) and [Ir(mppm)₂(accam)] (abbreviation) being 0.8:0.2:0.025. The thickness of the light-emitting layer 1113 was 40 nm.

Then, over the light-emitting layer 1113, 2mDBTPDBq-II (abbreviation) was deposited by evaporation to a thickness of 10 nm and then bathophenanthroline (abbreviation: Bphen) was deposited by evaporation to a thickness of 20 nm, whereby the electron-transport layer 1114 having a stacked structure was formed. Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form a second electrode 1103 serving as a cathode; thus, the light-emitting element 1 was obtained. Note that in all the above evaporation steps, evaporation was performed by a resistance-heating method.

An element structure of the light-emitting element 1 obtained as described above is shown in Table 1.

TABLE 1

|  | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 1 | ITSO (110 nm) | DBT3P-II:MoOx (4:2 40 nm) | BPAFLP (20 nm) | * | ** | Bphen (20 nm) | LiF (1 nm) | Al (200 nm) |

* 2mDBTPDBq-II:PCBA1BP:[Ir(mppm)$_2$(accam)] (0.8:0.2:0.025 40 nm)
** 2mDBTPDBq-II (10nm)

Further, the fabricated light-emitting element 1 was sealed in a glove box containing a nitrogen atmosphere so as not to be exposed to the air.

《Operation Characteristics of Light-Emitting Element 1》

Operation characteristics of the fabricated light-emitting element 1 were measured. Note that the measurement was carried out at room temperature (under an atmosphere in which the temperature was kept at 25° C.).

Figure 18:
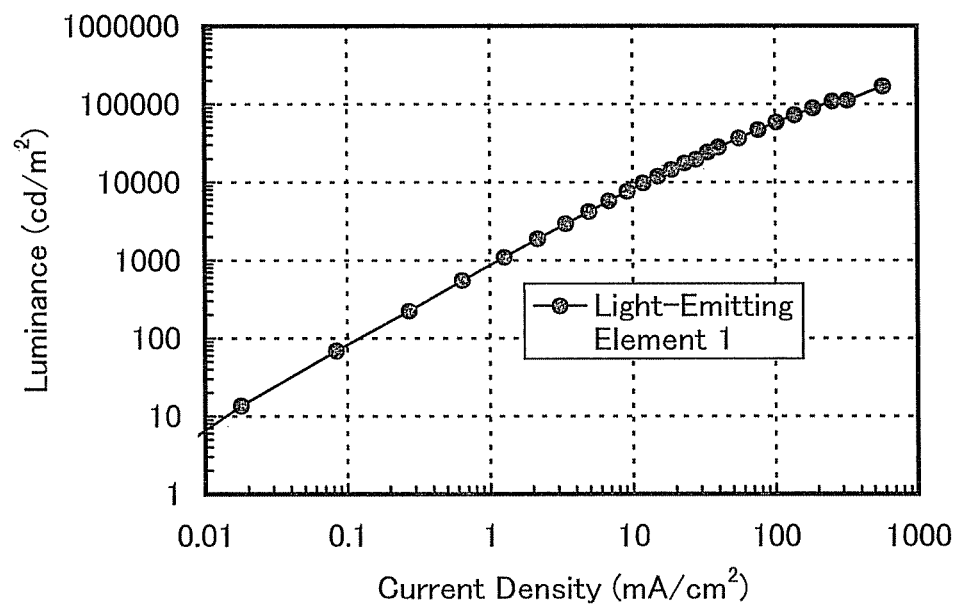
FIG. 18 shows current density-luminance characteristics of a light-emitting element 1.
Figure 19:
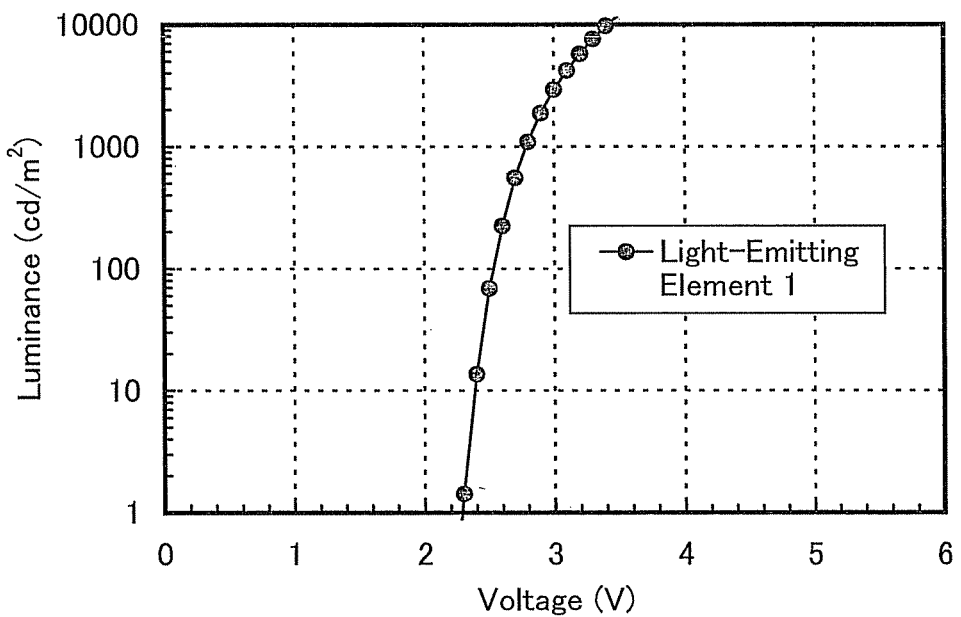
FIG. 19 shows voltage-luminance characteristics of a light-emitting element 1.
Figure 20:
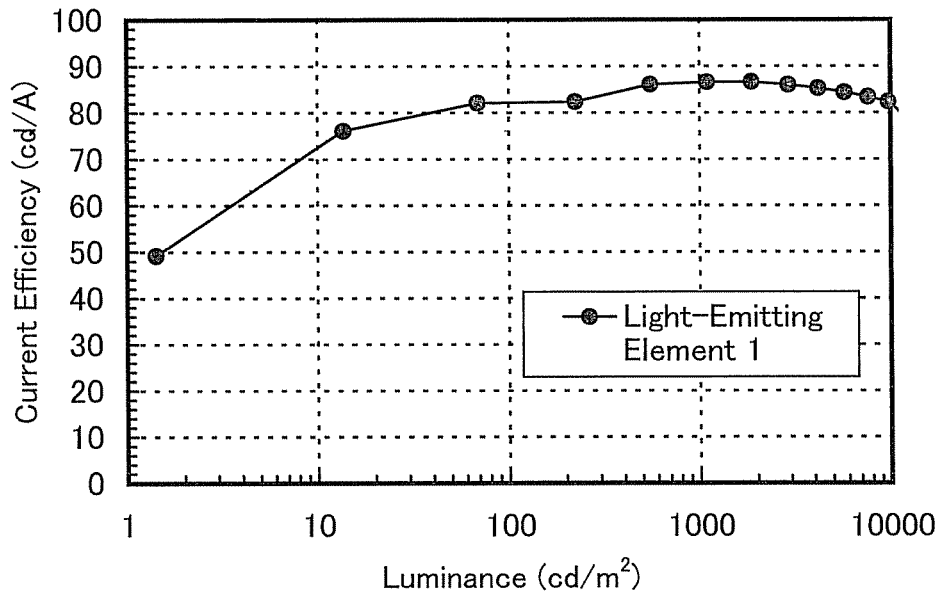
FIG. 20 shows luminance-current efficiency characteristics of a light-emitting element 1.
Figure 21:
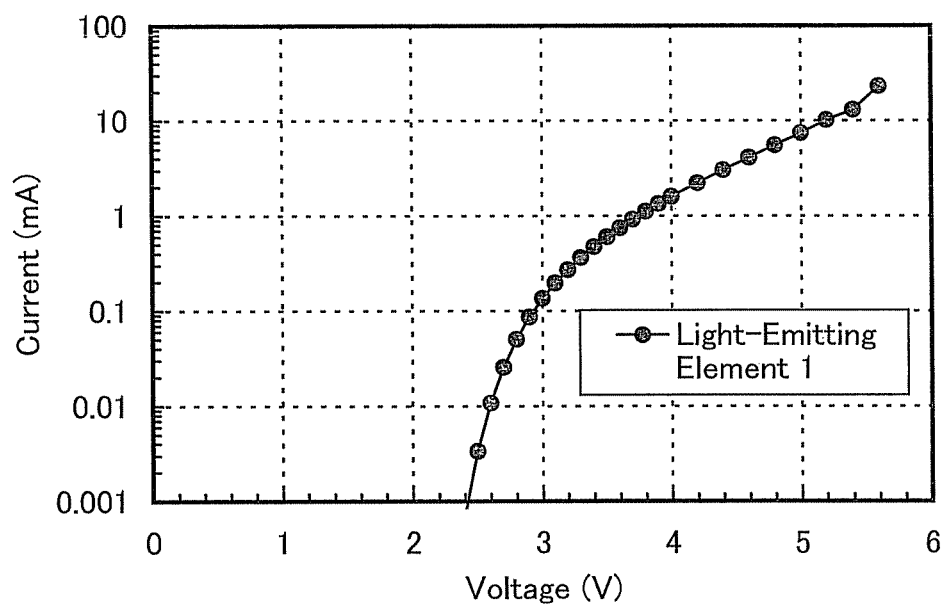
FIG. 21 shows voltage-current characteristics of a light-emitting element 1.

FIG. 18 shows current density-luminance characteristics of the light-emitting element 1. In FIG. 18, the vertical axis represents luminance (cd/m$^2$) and the horizontal axis represents current density (mA/cm$^2$). FIG. 19 shows voltage-luminance characteristics of the light-emitting element 1. In FIG. 19, the vertical axis represents luminance (cd/m$^2$) and the horizontal axis represents voltage (V). Further, FIG. 20 shows luminance-current efficiency characteristics of the light-emitting element 1. In FIG. 20, the vertical axis represents current efficiency (cd/A) and the horizontal axis represents luminance (cd/m$^2$). FIG. 21 shows voltage-current characteristics of the light-emitting element 1. In FIG. 21, the vertical axis represents current (mA) and the horizontal axis represents voltage (V).

FIG. 20 reveals high efficiency of the light-emitting element 1 in which part of the light-emitting layer uses [Ir(mppm)$_2$(accam)] (abbreviation), the phosphorescent organometallic iridium complex that is one embodiment of the present invention. Table 2 shows initial values of main characteristics of the light-emitting element at a luminance of about 1000 cd/m$^2$.

TABLE 2

|  | Voltage (V) | Current (mA) | Current Density (mA/cm$^2$) | Chromaticity (x, y) | Luminance (cd/m$^2$) | Current Efficiency (cd/A) | Power Efficiency (lm/W) | Quantum Efficiency (%) |
|---|---|---|---|---|---|---|---|---|
| Light-emitting Element 1 | 2.8 | 0.05 | 1.3 | (0.43, 0.56) | 1100 | 86.6 | 97.1 | 23.2 |

The above results show that the light-emitting element 1 fabricated in this example is a high-luminance light-emitting element having high current efficiency. Moreover, as for color purity, it can be found that the light-emitting element exhibits yellow green light emission with excellent color purity.

Figure 22:
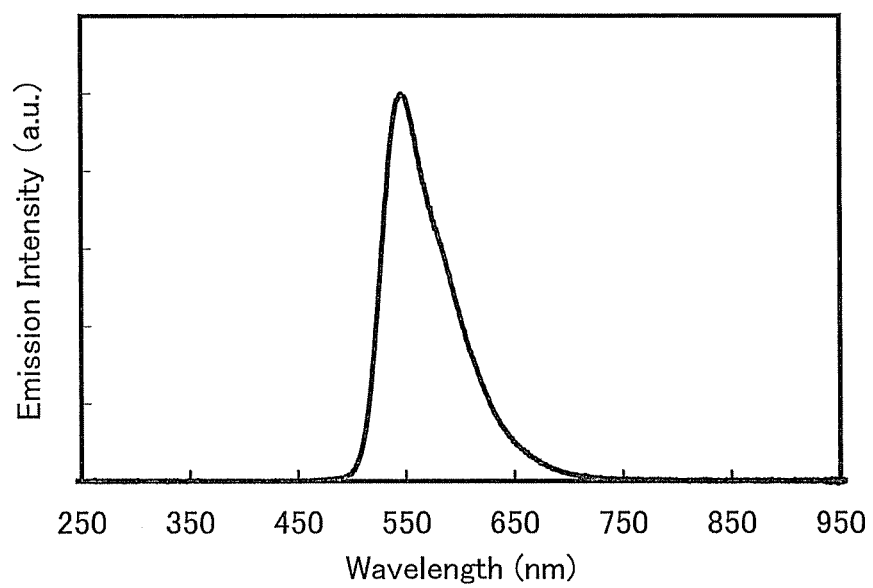
FIG. 22 shows an emission spectrum of a light-emitting element 1.

FIG. 22 shows an emission spectrum when a current at a current density of 2.5 mA/cm$^2$ was supplied to the light-emitting element 1. As shown in FIG. 22, the emission spectrum of the light-emitting element 1 has a peak at around 550 nm and it is indicated that the peak is derived from emission of the phosphorescent organometallic iridium complex [Ir(mppm)$_2$(accam)] (abbreviation).

Example 6

In this example, a light-emitting element 2 in which [Ir(mppm)$_2$(achex)] (abbreviation), the phosphorescent organometallic iridium complex represented by Structural Formula (101), is used for a light-emitting layer is described. Note that in the description of the light-emitting element 2 in this example, FIG. 17 which is used in the description of the light-emitting element 1 in Example 5 is to be referred to. Chemical formulae of materials used in this example are shown below.

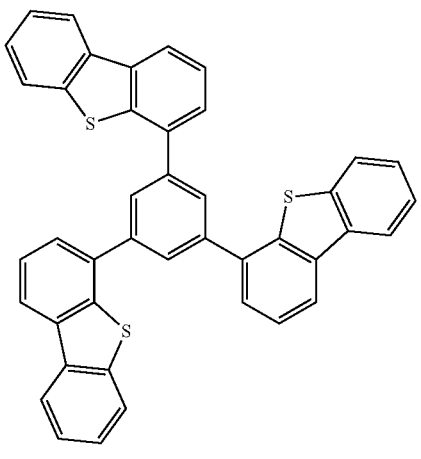

DBT3P-II

-continued

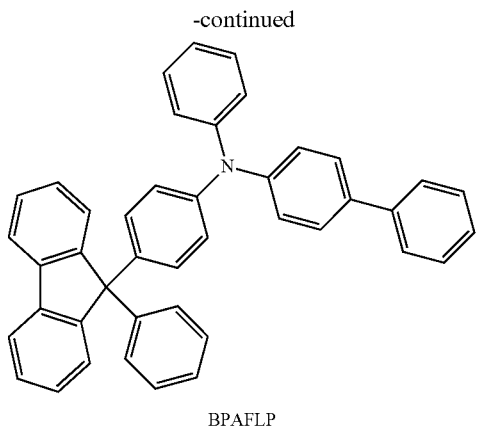

BPAFLP

-continued

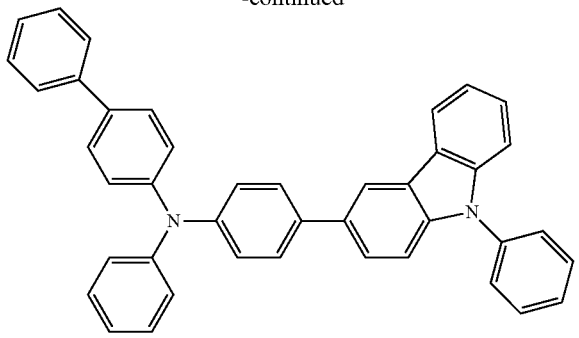

PCBA1BP

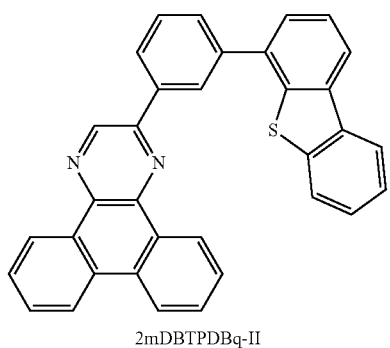

2mDBTPDBq-II

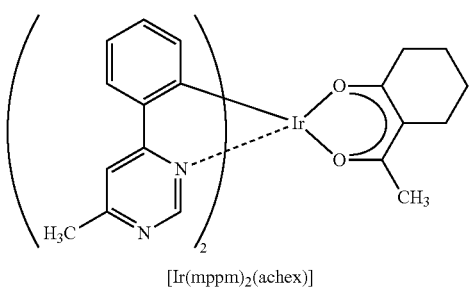

[Ir(mppm)₂(achex)]

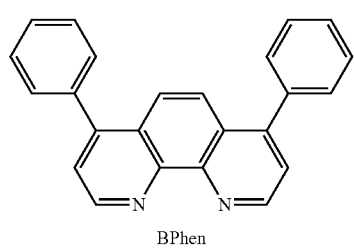

BPhen

《Fabrication of Light-Emitting Element 2》

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm.

Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were co-evaporated with a mass ratio of DBT3P-II (abbreviation) to molybdenum oxide being 4:2, whereby the hole-injection layer 1111 was formed over the first electrode 1101. The thickness of the hole-injection layer 1111 was 40 nm. Note that the co-evaporation is an evaporation method in which some different substances are evaporated, from some different evaporation sources at the same time.

Then, 4-phenyl-4'-(9-phenylfluoren-9-yl)triphenylamine (abbreviation: BPAFLP) was deposited by evaporation to a thickness of 20 nm, so that the hole-transport layer 1112 was formed.

Next, the light-emitting layer 1113 was formed over the hole-transport layer 1112 in the following manner. Co-evaporated were 2-[3-(dibenzothiophen-4-yl)phenyl]dibenzo[f,h]quinoxaline (abbreviation: 2mDBTPDBq-II), 4-phenyl-4'-(9-phenyl-9H-carbazol-3-yl)triphenylamine (abbreviation: PCBA1BP), and [2-(acetyl-κO)-cyclohexanonato-κO]bis[2-(3-methyl-4-pyrimidinyl-κN3)phenyl-κC]iridium(III) (abbreviation: [Ir(mppm)₂(achex)]) with a mass ratio of 2mDBTPDBq-II (abbreviation) to PCBA1BP (abbreviation) and [Ir(mppm)₂(achex)] (abbreviation) being 0.8:0.2:0.025. The thickness of the light-emitting layer 1113 was 40 nm.

Then, over the light-emitting layer 1113, 2mDBTPDBq-II (abbreviation) was deposited by evaporation to a thickness of 10 nm and then bathophenanthroline (abbreviation: Bphen) was deposited by evaporation to a thickness of 20 nm, whereby the electron-transport layer 1114 having a stacked structure was formed. Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form the second electrode 1103 serving as a cathode; thus, the light-emitting element 2 was obtained. Note that in all the above evaporation steps, evaporation was performed by a resistance-heating method.

An element structure of the light-emitting element 2 obtained as described above is shown in Table 3.

TABLE 3

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 2 | ITSO (110 nm) | DBT3P-II:MoOx (4:2 40 nm) | BPAFLP (20 nm) | * | ** | Bphen (20 nm) | LiF (1 nm) | Al (200 nm) |

* 2mDBTPDBq-II:PCBA1BP:[Ir(mppm)₂(achex)] (0.8:0.2:0.025 40 nm)
** 2mDBTPDBq-II (10 nm)

Further, the fabricated light-emitting element 2 was sealed in a glove box containing a nitrogen atmosphere so as not to be exposed to the air.

《Operation Characteristics of Light-Emitting Element 2》

Operation characteristics of the fabricated light-emitting element 2 were measured. Note that the measurement was carried out at room temperature (under an atmosphere in which the temperature was kept at 25° C.).

Figure 23:
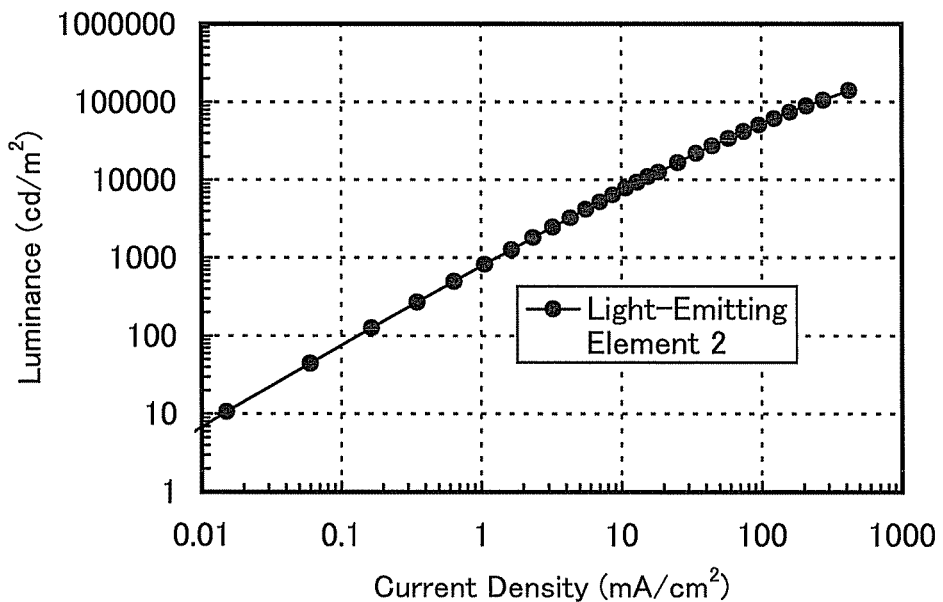
FIG. 23 shows current density-luminance characteristics of a light-emitting element 2.
Figure 24:
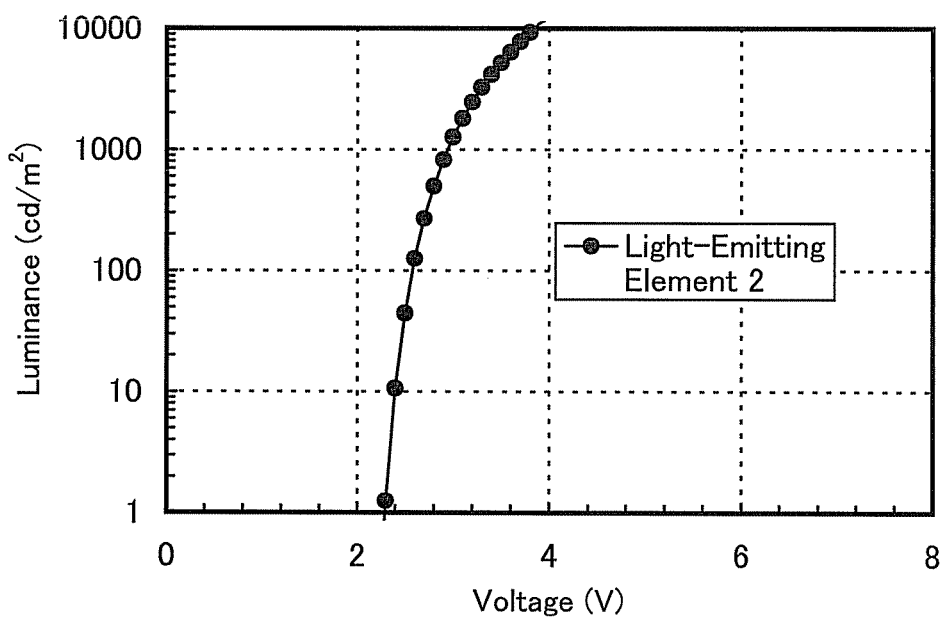
FIG. 24 shows voltage-luminance characteristics of a light-emitting element 2.
Figure 25:
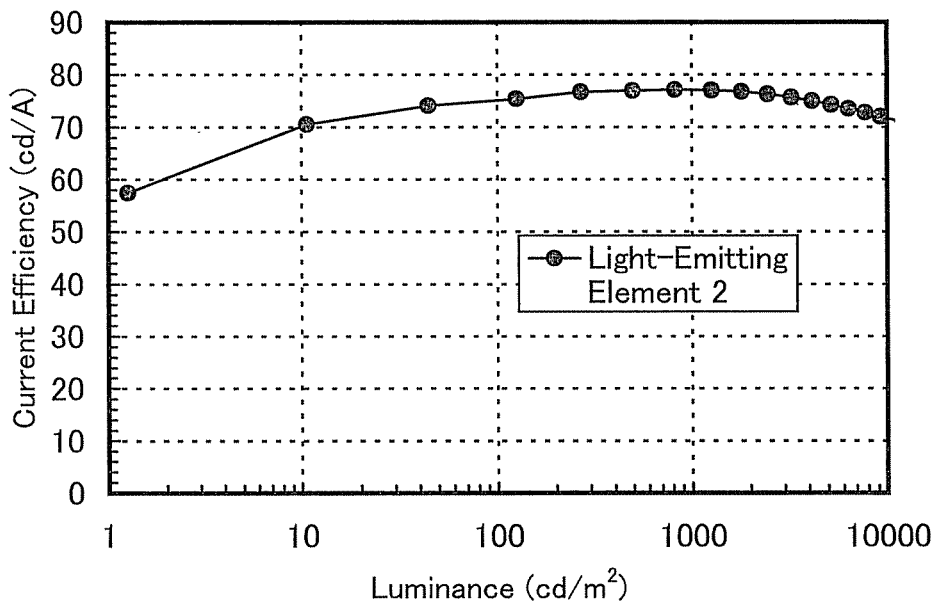
FIG. 25 shows luminance-current efficiency characteristics of a light-emitting element 2.
Figure 26:
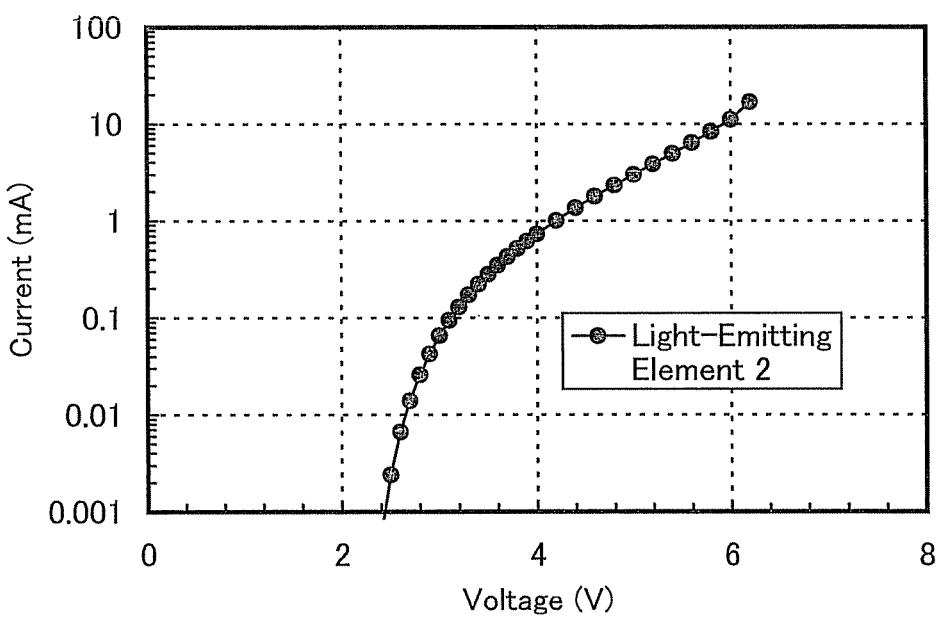
FIG. 26 shows voltage-current characteristics of a light-emitting element 2.

FIG. 23 shows current density-luminance characteristics of the light-emitting element 2. In FIG. 23, the vertical axis represents luminance (cd/m²) and the horizontal axis represents current density (mA/cm²). FIG. 24 shows voltage-luminance characteristics of the light-emitting element 2. In FIG. 24, the vertical axis represents luminance (cd/m²) and the horizontal axis represents voltage (V). Further, FIG. 25 shows luminance-current efficiency characteristics of the light-emitting element 2. In FIG. 25, the vertical axis represents current efficiency (cd/A) and the horizontal axis represents luminance (cd/m²). FIG. 26 shows voltage-current characteristics of the light-emitting element 2. In FIG. 26, the vertical axis represents current (mA) and the horizontal axis represents voltage (V).

FIG. 25 reveals high efficiency of the light-emitting element 2 in which part of the light-emitting layer uses [Ir(mppm)₂(achex)] (abbreviation), the phosphorescent organometallic iridium complex that is one embodiment of the present invention. Table 4 shows initial values of main characteristics of the light-emitting element at a luminance of about 1000 cd/m².

TABLE 4

| | Voltage (V) | Current (mA) | Current Density (mA/cm²) | Chromaticity (x, y) | Luminance (cd/m²) | Current Efficiency (cd/A) | Power Efficiency (lm/W) | Quantum Efficiency (%) |
|---|---|---|---|---|---|---|---|---|
| Light-emitting Element 2 | 2.9 | 0.043 | 1.1 | (0.46, 0.53) | 820 | 77 | 84 | 22 |

The above results show that the light-emitting element 2 fabricated in this example is a high-luminance light-emitting element having high current efficiency. Moreover, as for color purity, it can be found that the light-emitting element exhibits yellow green light emission with excellent color purity.

Figure 27:
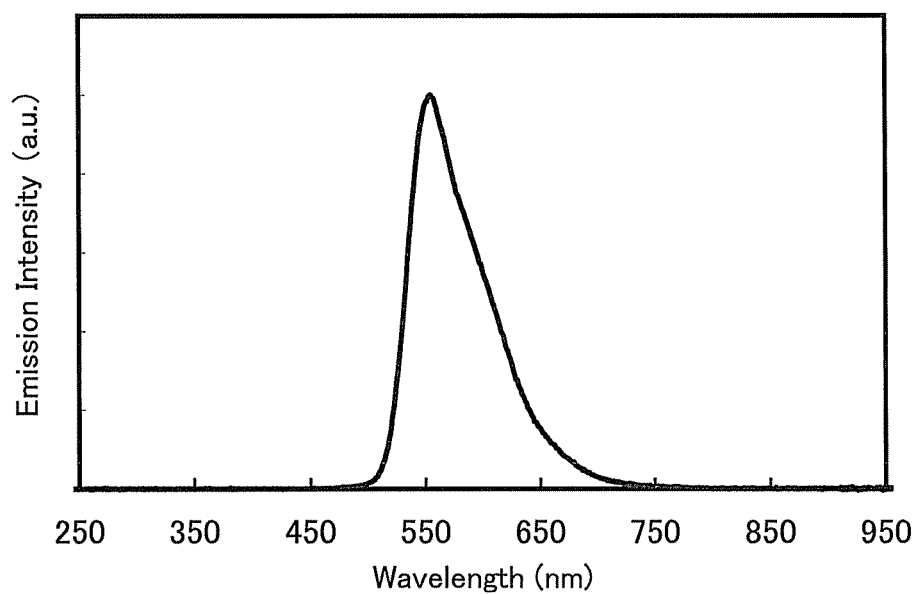
FIG. 27 shows an emission spectrum of a light-emitting element 2.

FIG. 27 shows an emission spectrum when a current at a current density of 2.5 mA/cm² was supplied to the light-emitting element 2. As shown in FIG. 27, the emission spectrum of the light-emitting element 2 has a peak at around 560 nm and it is indicated that the peak is derived from emission of the phosphorescent organometallic iridium complex [Ir(mppm)₂(achex)] (abbreviation).

Example 7

In this example, a light-emitting element 3 in which [Ir(mppm)₂(acpen)] (abbreviation), the phosphorescent organometallic iridium complex represented by Structural Formula (104), is used for a light-emitting layer is described. Note that in the description of the light-emitting element 3 in this example, FIG. 17 which is used in the description of the light-emitting element 1 in Example 5 is to be referred to. Chemical formulae of materials used in this example are shown below.

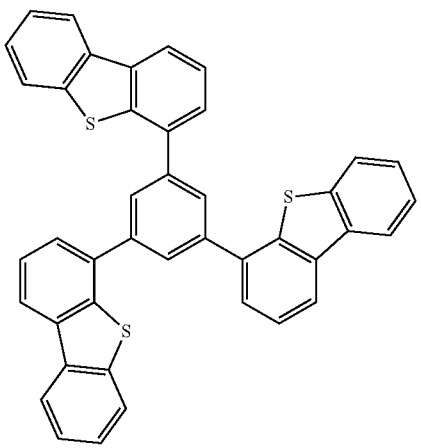

DBT3P-II

-continued

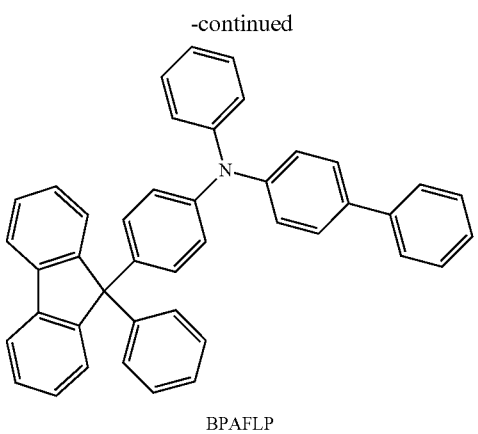

BPAFLP

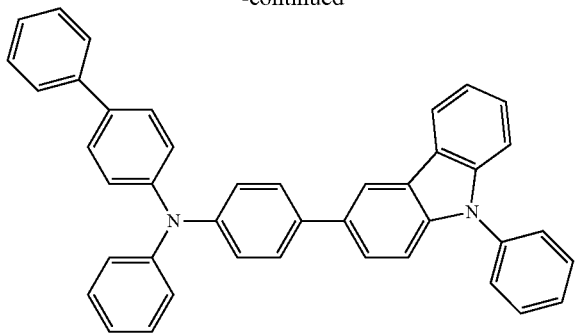

PCBA1BP

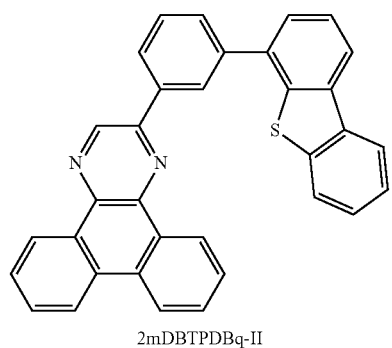

2mDBTPDBq-II

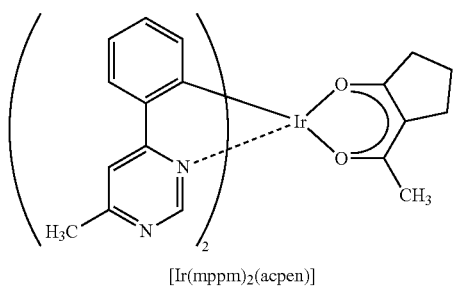

[Ir(mppm)₂(acpen)]          (104)

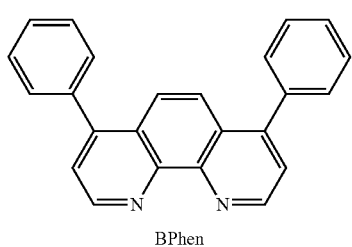

BPhen

《Fabrication of Light-Emitting Element 3》

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm.

Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were co-evaporated with a mass ratio of DBT3P-II (abbreviation) to molybdenum oxide being 4:2, whereby the hole-injection layer 1111 was formed over the first electrode 1101. The thickness of the hole-injection layer 1111 was 40 nm. Note that the co-evaporation is an evaporation method in which some different substances are evaporated from some different evaporation sources at the same time.

Then, 4-phenyl-4'-(9-phenylfluoren-9-yl)triphenylamine (abbreviation: BPAFLP) was deposited by evaporation to a thickness of 20 nm, so that the hole-transport layer 1112 was formed.

Next, the light-emitting layer 1113 was formed over the hole-transport layer 1112 in the following manner. Co-evaporated were 2-[3-(dibenzothiophen-4-yl)phenyl]dibenzo[f,h]quinoxaline (abbreviation: 2mDBTPDBq-II), 4-phenyl-4'-(9-phenyl-9H-carbazol-3-yl)triphenylamine (abbreviation: PCBA1BP), and [2-(acetyl-κO)-cyclopentanonato-κO]bis[2-(6-methyl-4-pyrimidinyl-κN3)phenyl-κC]iridium(III) (abbreviation: [Ir(mppm)₂(acpen)]) with a mass ratio of 2mDBTPDBq-II (abbreviation) to PCBA1BP (abbreviation) and [Ir(mppm)₂(acpen)] (abbreviation) being 0.8:0.2:0.025. The thickness of the light-emitting layer 1113 was 40 nm.

Then, over the light-emitting layer 1113, 2mDBTPDBq-II (abbreviation) was deposited by evaporation to a thickness of 10 nm and then bathophenanthroline (abbreviation: Bphen) was deposited by evaporation to a thickness of 20 nm, whereby the electron-transport layer 1114 having a stacked structure was formed. Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form the second electrode 1103 serving as a cathode; thus, the light-emitting element 3 was obtained. Note that in all the above evaporation steps, evaporation was performed by a resistance-heating method.

An element structure of the light-emitting element 3 obtained as described above is shown in Table 5.

TABLE 5

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 3 | ITSO (110 nm) | DBT3P-II:MoOx (4:2 40 nm) | BPAFLP (20 nm) | * | ** | Bphen (20 nm) | LiF (1 nm) | Al (200 nm) |

* 2mDBTPDBq-II:PCBA1BP:[Ir(mppm)$_2$(acpen)] (0.8:0.2:0.025 40 nm)
** 2mDBTPDBq-II (10 nm)

Further, the fabricated light-emitting element 3 was sealed in a glove box containing a nitrogen atmosphere so as not to be exposed to the air.

《Operation Characteristics of Light-Emitting Element 3》

Operation characteristics of the fabricated light-emitting element 3 were measured. Note that the measurement was carried out at room temperature (under an atmosphere in which the temperature was kept at 25° C.).

Figure 28:
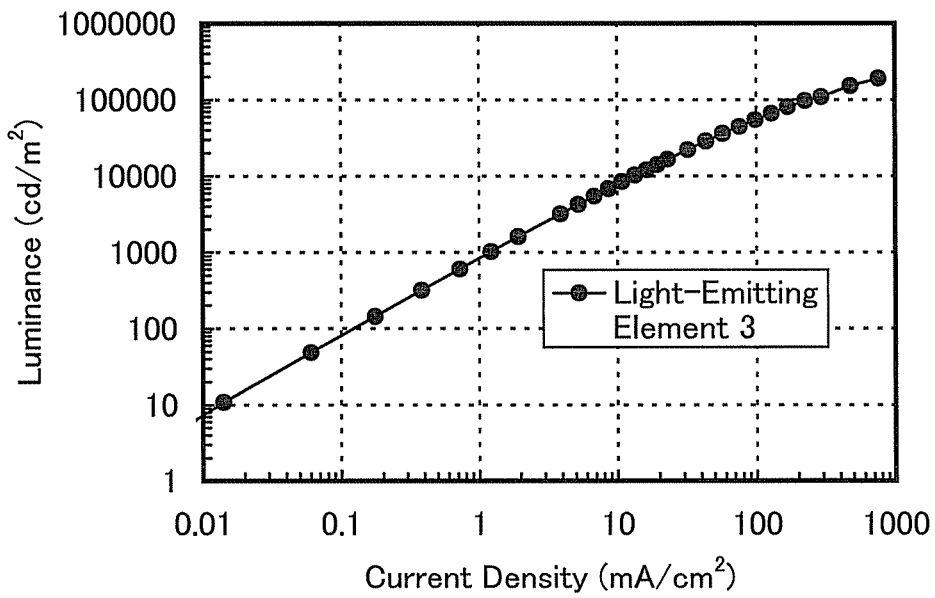
FIG. 28 shows current density-luminance characteristics of a light-emitting element 3.
Figure 29:
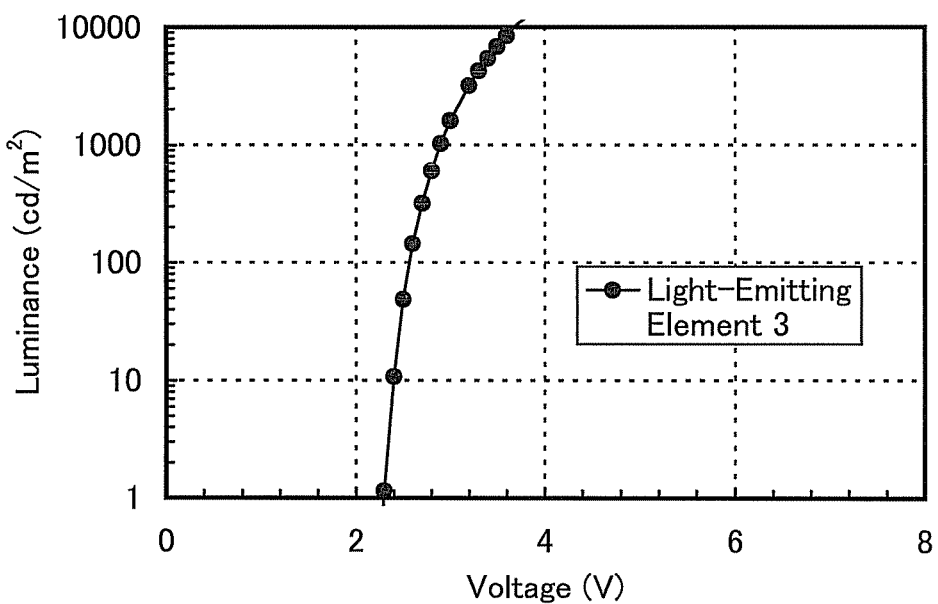
FIG. 29 shows voltage-luminance characteristics of a light-emitting element 3.
Figure 30:
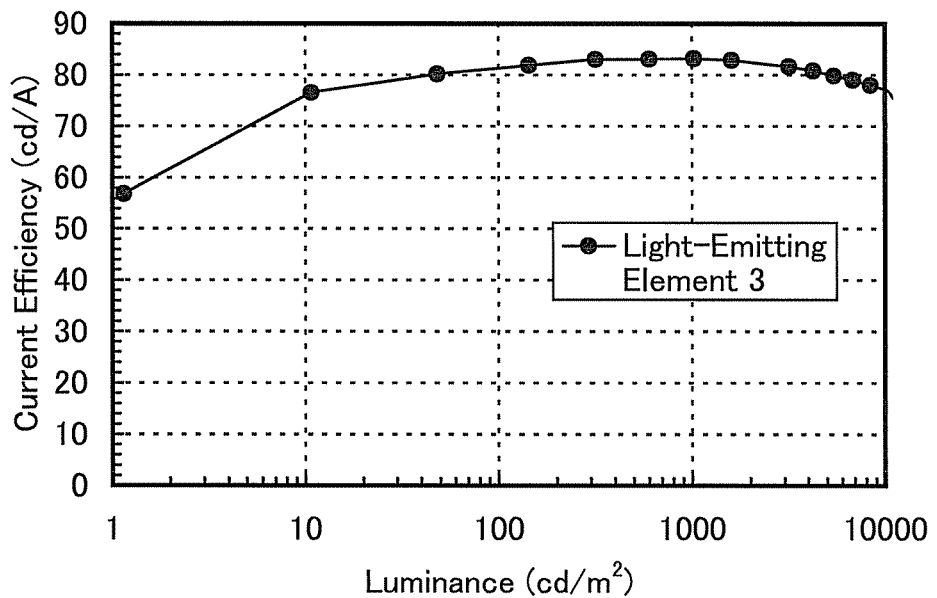
FIG. 30 shows luminance-current efficiency characteristics of a light-emitting element 3.
Figure 31:
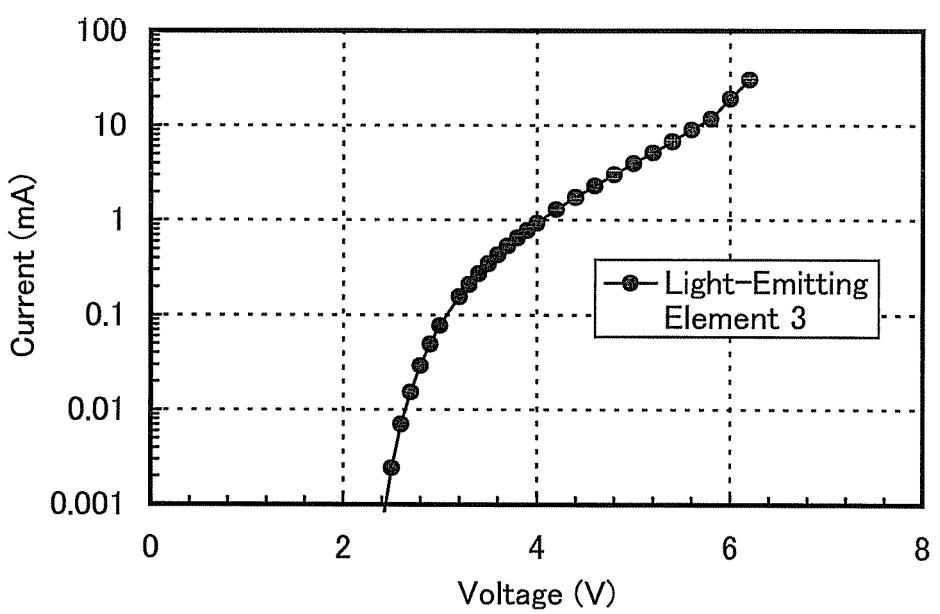
FIG. 31 shows voltage-current characteristics of a light-emitting element 3.

FIG. 28 shows current density-luminance characteristics of the light-emitting element 3. In FIG. 28, the vertical axis represents luminance (cd/m$^2$) and the horizontal axis represents current density (mA/cm$^2$). FIG. 29 shows voltage-luminance characteristics of the light-emitting element 3. In FIG. 29, the vertical axis represents luminance (cd/m$^2$) and the horizontal axis represents voltage (V). Further, FIG. 30 shows luminance-current efficiency characteristics of the light-emitting element 3. In FIG. 30, the vertical axis represents current efficiency (cd/A) and the horizontal axis represents luminance (cd/m$^2$). FIG. 31 shows voltage-current characteristics of the light-emitting element 3. In FIG. 31, the vertical axis represents current (mA) and the horizontal axis represents voltage (V).

FIG. 30 reveals high efficiency of the light-emitting element 3 in which part of the light-emitting layer uses [Ir(mppm)$_2$(acpen)] (abbreviation), the phosphorescent organometallic iridium complex that is one embodiment of the present invention. Table 6 shows initial values of main characteristics of the light-emitting element at a luminance of about 1000 cd/m$^2$.

TABLE 6

| | Voltage (V) | Current (mA) | Current Density (mA/cm$^2$) | Chromaticity (x, y) | Luminance (cd/m$^2$) | Current Efficiency (cd/A) | Power Efficiency (lm/W) | Quantum Efficiency (%) |
|---|---|---|---|---|---|---|---|---|
| Light-emitting Element 3 | 2.9 | 0.049 | 1.2 | (0.43, 0.56) | 1000 | 83 | 90 | 23 |

The above results show that the light-emitting element 3 fabricated in this example is a high-luminance light-emitting element having high current efficiency. Moreover, as for color purity, it can be found that the light-emitting element exhibits yellow green light emission with excellent color purity.

Figure 32:
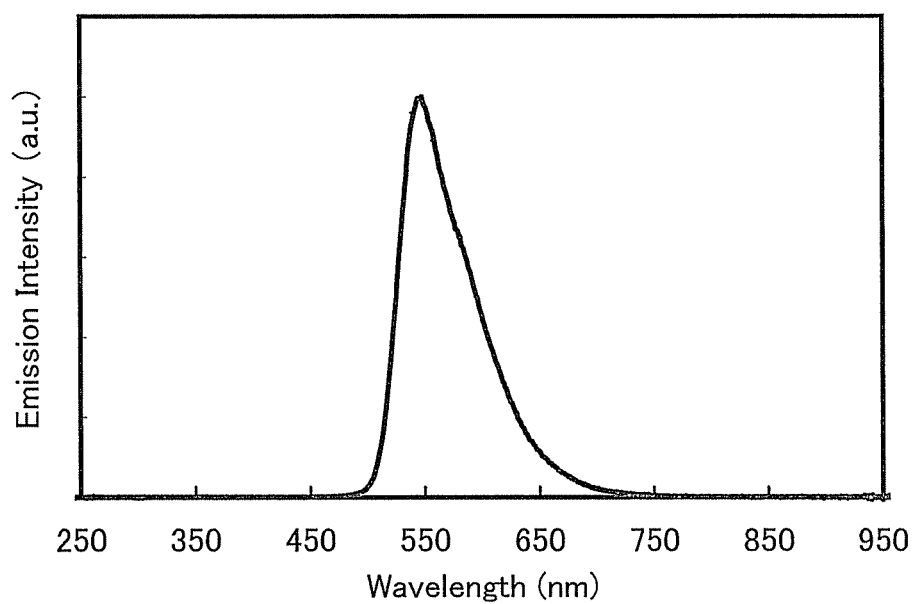
FIG. 32 shows an emission spectrum of a light-emitting element 3.

FIG. 32 shows an emission spectrum when a current at a current density of 2.5 mA/cm$^2$ was supplied to the light-emitting element 3. As shown in FIG. 32, the emission spectrum of the light-emitting element 3 has a peak at around 550 nm and it is indicated that the peak is derived from emission of the phosphorescent organometallic iridium complex [Ir(mppm)$_2$(acpen)] (abbreviation).

This application is based on Japanese Patent Application serial no. 2011-261289 filed with Japan Patent Office on Nov. 30, 2011, the entire contents of which are hereby incorporated by reference.

What is claimed is:

1. An organometallic complex represented by Formula (G2) or Formula (G3),

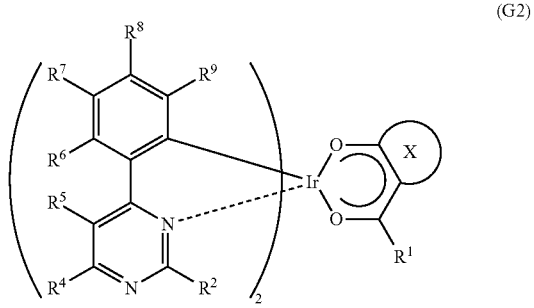

(G2)

-continued

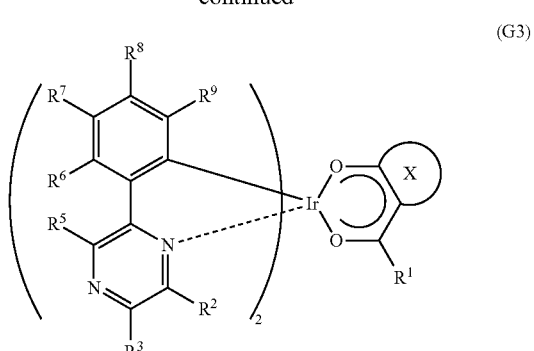

(G3)

wherein:

X represents a five-membered or six-membered alicycle composed of carbon and hydrogen, $R^1$ represents an alkyl group having 1 to 4 carbon atoms, and $R^2, R^3, R^4, R^5, R^6, R^7, R^8$, and $R^9$ independently represent an alkyl group having 1 to 4 carbon atoms or a phenyl group.

2. The organometallic complex according to claim 1, wherein the organometallic complex is represented by Formula (100) or Formula (104),

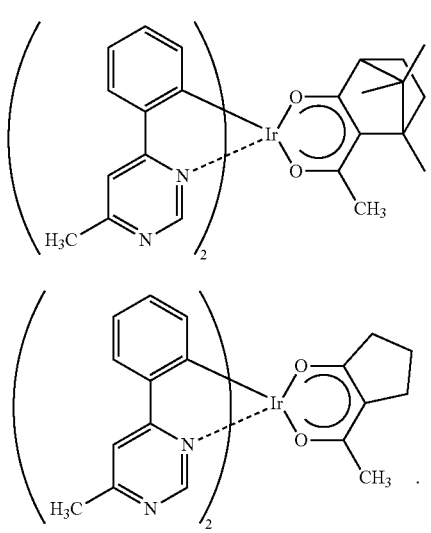

(100)

(104)

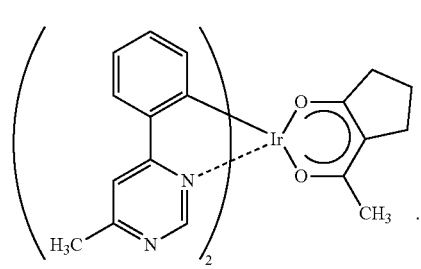

3. The organometallic complex according to claim 1, wherein the alicycle is intramolecularly bridged.

4. An organometallic complex represented by Formula (101),

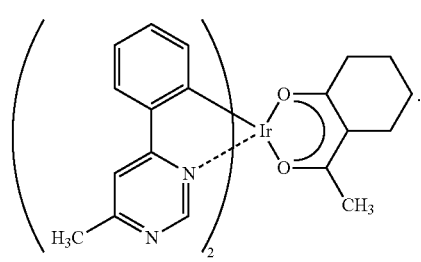

(101)

5. A light-emitting element comprising the organometallic complex according to claim 4.

6. A light-emitting device comprising the light-emitting element according to claim 5.

7. An electronic device comprising the light-emitting device according to claim 6.

8. A lighting device comprising the light-emitting device according to claim 6.

9. An organometallic complex represented by Formula (113),

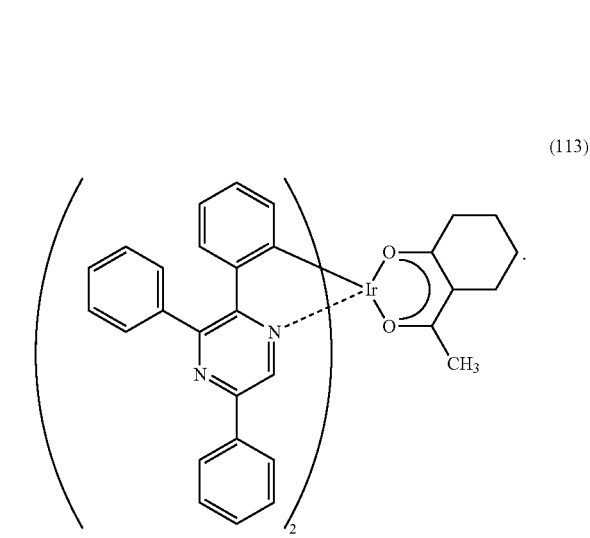

(113)

10. A light-emitting element comprising the organometallic complex according to claim 9.

11. A light-emitting device comprising the light-emitting element according to claim 10.

12. An electronic device comprising the light-emitting device according to claim 11.

13. A lighting device comprising the light-emitting device according to claim 11.

* * * * *

UNITED STATES PATENT AND TRADEMARK OFFICE
CERTIFICATE OF CORRECTION

PATENT NO. : 9,260,463 B2  
APPLICATION NO. : 13/688688  
DATED : February 16, 2016  
INVENTOR(S) : Hideko Inoue et al.

Page 1 of 2

It is certified that error appears in the above-identified patent and that said Letters Patent is hereby corrected as shown below:

In the Specification:

Column 4, Line 57, Formula (G3);
Change

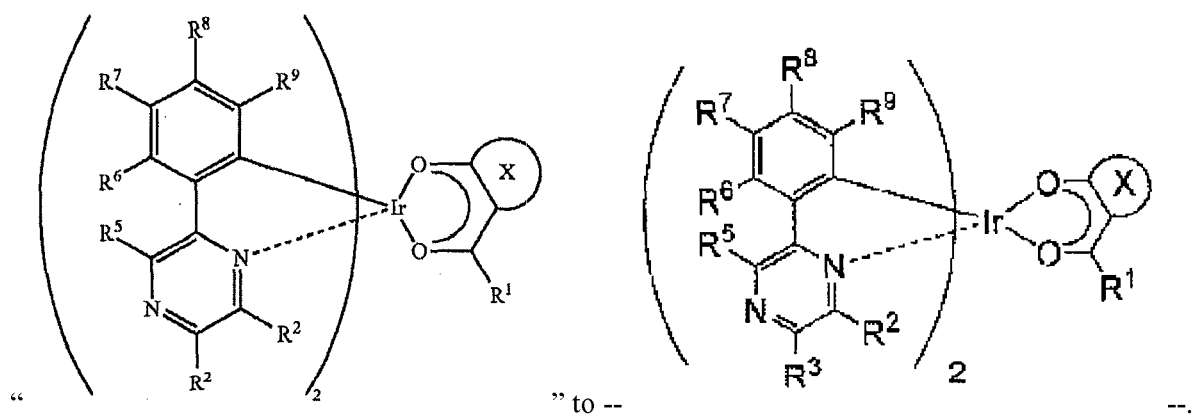

Column 4, Line 62; Change "allyl" to --alkyl--.

Column 20, Line 44; Change "like, can" to --like can--.

Column 20, Line 54; Change "PVK); poly" to --PVK), poly--.

Column 21, Line 24; Change "Alg$_3$," to --Alq$_3$,--.

Column 22, Line 54; Change "Further more," to --Furthermore,--.

Column 28, Line 27; Change "includes, a" to --includes a--.

Column 29, Line 15; Change "Light," to --Light--.

Column 30, Line 43; Change "light-emit/ting" to --light-emitting--.

Column 42, Line 51; Change "Japan," to --Japan--.

Column 43, Line 54; Change "di-β" to --di-μ--.

Signed and Sealed this  
Fifth Day of July, 2016

Michelle K. Lee  
*Director of the United States Patent and Trademark Office*

CERTIFICATE OF CORRECTION (continued)
U.S. Pat. No. 9,260,463 B2

In the Specification:

Column 54, Line 31; Change "evaporated, from" to --evaporated from--.

Column 59, Line 32; Change "horizontal, axis" to --horizontal axis--.